United States Patent
Aoyama et al.

(10) Patent No.: US 9,783,483 B2
(45) Date of Patent: Oct. 10, 2017

(54) PROCESS FOR PRODUCING FLUORINATED COMPOUND

(71) Applicant: Asahi Glass Company, Limited, Chiyoda-ku (JP)

(72) Inventors: Motoshi Aoyama, Chiyoda-ku (JP); Jumpei Nomura, Chiyoda-ku (JP)

(73) Assignee: Asahi Glass Company, Limited, Chiyoda-ku (JP)

(*) Notice: Subject to any disclaimer, the term of this patent is extended or adjusted under 35 U.S.C. 154(b) by 0 days.

(21) Appl. No.: 15/016,426

(22) Filed: Feb. 5, 2016

(65) Prior Publication Data

US 2016/0152545 A1 Jun. 2, 2016

Related U.S. Application Data

(63) Continuation of application No. PCT/JP2014/071673, filed on Aug. 19, 2014.

(30) Foreign Application Priority Data

Aug. 26, 2013 (JP) ................................. 2013-175041

(51) Int. Cl.
| | |
|---|---|
| *C07C 67/287* | (2006.01) |
| *C07C 67/14* | (2006.01) |
| *C07C 41/18* | (2006.01) |
| *C08F 116/12* | (2006.01) |
| *C07C 51/58* | (2006.01) |
| *C07C 41/24* | (2006.01) |
| *C08F 216/12* | (2006.01) |
| *C08F 216/14* | (2006.01) |

(52) U.S. Cl.
CPC ............ *C07C 67/287* (2013.01); *C07C 41/18* (2013.01); *C07C 41/24* (2013.01); *C07C 51/58* (2013.01); *C07C 67/14* (2013.01); *C08F 116/12* (2013.01); *C08F 216/1408* (2013.01)

(58) Field of Classification Search
CPC ....... C07C 67/14; C07C 67/287; C07C 69/63; C08F 116/12

USPC ............ 560/192; 562/850; 568/685; 526/75, 526/292.3, 292.9
See application file for complete search history.

(56) References Cited

U.S. PATENT DOCUMENTS

| | | |
|---|---|---|
| 2003/0135067 A1 | 7/2003 | Okazoe et al. |
| 2006/0030733 A1 | 2/2006 | Wang et al. |

FOREIGN PATENT DOCUMENTS

| | | |
|---|---|---|
| JP | 2004-346014 | 12/2004 |
| WO | WO 02/04397 A1 | 1/2002 |
| WO | WO 2004/080940 A1 | 9/2004 |

OTHER PUBLICATIONS

Okazoe, et al, Synthesis of perfluorinated carboxylic acid membrane monomers by utilizing liquid-phase direct fluorination, Journal of Fluorine Chemistry, 126 (2005) 521-527.*
English Translation of International Search Report dated Nov. 11, 2014 in PCT/JP2014/071673, filed Aug. 19, 2014.
Masaaki Yamabe et al. "Synthesis of Perfluorinated Vinyl Ethers Having Ester Group", Journal of Fluorine Chemistry, vol. 94, 1999, 3 pages.

* cited by examiner

*Primary Examiner* — Fred M Teskin
(74) *Attorney, Agent, or Firm* — Oblon, McClelland, Maier & Neustadt, L.L.P.

(57) ABSTRACT

To provide a process for producing a desired perfluorinated product at a high yield in a fluorination reaction of a partially fluorinated ester.

A perfluorinated compound (4) is obtained by fluorinating in a liquid phase a compound (3) (wherein the fluorine content is at least 30 mass %) obtained by reacting a compound (1) and a compound (2), wherein the compound (1) is $HOCH_2—R^A—CH_2OH$, the compound (2) is $X^1C(=O)—C(R^B)(R^C)(R^D)$, $R^A$ is a bivalent saturated hydrocarbon group or the like which has no hetero atom such as an etheric oxygen atom, $X^1$ is a halogen atom, and $—C(R^B)(R^C)(R^D)$ is a branched group.

16 Claims, No Drawings

PROCESS FOR PRODUCING FLUORINATED COMPOUND

TECHNICAL FIELD

The present invention relates to a process for producing an industrially useful fluorinated compound.

BACKGROUND ART

A fluorinated monomer such as a perfluoro(alkyl vinyl ether) is useful as a starting material monomer for a fluorinated resin which is excellent in heat resistance and chemical resistance. For example, a perfluoro(alkyl vinyl ether) having a carboxy group in its molecule is useful as a starting material monomer for an ion exchange membrane and is produced via a diacyl fluoride (Non-Patent Document 1).

As the process for producing a diacyl fluoride used for producing a fluorinated monomer, a process having the following steps (1) to (3) has been known (Patent Document 1).

Step (1): A step of reacting a bifunctional alcohol with a monoacyl fluoride to obtain a partially fluorinated ester.

Step (2): A step of obtaining a perfluoroester from the partially fluorinated ester by a fluorination reaction.

Step (3): A step of obtaining a diacyl fluoride by a decomposition reaction of the perfluoroester.

PRIOR ART DOCUMENTS

Patent Document

Patent Document 1: WO2002/004397

Patent Document

Non-Patent Document 1: J. Fluorine Chem., 94, 65-68 (1999)

DISCLOSURE OF INVENTION

Technical Problem

However, in the production process described in Patent Document 1, the yield of the perfluoroester in the above step (2) is low.

It is an object of the present invention to provide a process for producing a desired perfluorinated compound in good yield in a fluorination reaction of a partially fluorinated ester.

Solution to Problem

The present invention provides a process for producing a fluorinated compound having the following constructions [1] to [14].

[1] A process for producing a fluorinated compound, which comprises a step (I) of reacting a compound (1) represented by the following formula (1) and a compound (2) represented by the following formula (2) to produce a compound (3) represented by the following formula (3) (wherein the fluorine content is at least 30 mass %) and a step (II) of fluorinating the compound (3) in a liquid phase to produce a compound (4) represented by the following formula (4), $$HOCH_2-R^A-CH_2OH \quad (1)$$

$$X^1C(=O)-C(R^B)(R^C)(R^D) \quad (2)$$

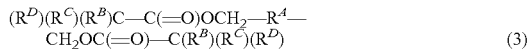  (3)

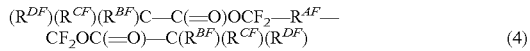  (4)

wherein $R^A$: a bivalent saturated hydrocarbon group or a partially halogenated bivalent saturated hydrocarbon group, $R^B$, $R^C$ and $R^D$: $R^B$ is the same fluorinated monovalent organic group as $R^{BF}$, a monovalent organic group to be converted to $R^{BF}$ by a fluorination reaction, a hydrogen atom or a halogen atom; $R^C$ is the same fluorinated monovalent organic group as $R^{CF}$ or a monovalent organic group to be converted to $R^{CF}$ by a fluorination reaction; and $R^D$ is the same fluorinated monovalent organic group as $R^{DF}$ or a monovalent organic group to be converted to $R^{DF}$ by a fluorination reaction, $X^1$: a halogen atom, $R^{AF}$: a group having all hydrogen atoms in $R^A$ substituted by fluorine atoms, $R^{BF}$: when $R^B$ is a hydrogen atom, $R^{BF}$ is a fluorine atom; when $R^B$ is a halogen atom, $R^{BF}$ is the same halogen atom as $R^B$; and when $R^B$ is neither a hydrogen atom nor a halogen atom, $R^{BF}$ is a fluorinated monovalent organic group which is the same as or different from $R^B$, and when different, $R^{BF}$ is a group which is $R^B$ fluorinated, $R^{CF}$: a monovalent fluorinated organic group which is the same as or different from $R^C$, and when different, $R^{CF}$ is a group which is $R^C$ fluorinated, and $R^{DF}$: a fluorinated monovalent organic group which is the same as or different from $R^D$, and when different, $R^{DF}$ is a group which is $R^D$ fluorinated.

[2] The process for producing a fluorinated compound according to [1], wherein the number of carbon atoms of $R^A$ is at most 20, and when each of $R^B$, $R^C$ and $R^D$ is the fluorinated monovalent organic group or the monovalent organic group, the number of carbon atoms thereof is at most 10.

[3] The process for producing a fluorinated compound according to [1] or [2], wherein $R^A$ is $(CH_2)_n$, and $R^{AF}$ is $(CF_2)_n$ (wherein n is an integer of from 1 to 10).

[4] The process for producing a fluorinated compound according to any one of [1] to [3], wherein $R^B$ and $R^{BF}$ are fluorine atoms, $R^C$ and $R^{CF}$ are the same $C_{1-3}$ perfluoroalkyl groups, and $R^D$ and $R^{DF}$ are the same $C_1$ perfluoroalkyl groups, the same $C_{2-6}$ perfluoroalkoxyl groups or the same $C_{4-8}$ perfluoroalkoxyl groups having one etheric oxygen atom.

[5] The process for producing a fluorinated compound according to any one of [1] to [4], wherein in the step (II), the fluorination is carried out by supplying a fluorine gas diluted with an inert gas, into the liquid phase, and the proportion of the fluorine gas is from 30 to 60 vol % in the total 100 vol % of the inert gas and the fluorine gas.

[6] The process for producing a fluorinated compound according to any one of [1] to [5], wherein the fluorination is carried out in the liquid phase containing a fluorination reaction solvent, and the fluorination reaction solvent is a fluorinated solvent having no C—H bond and having an etheric oxygen atom.

[7] The process for producing a fluorinated compound according to [6], wherein the fluorinated solvent is $(R^{DF})(R^{CF})(R^{BF})C-C(=O)F$, wherein $R^{BF}$, $R^{CF}$ and $R^{DF}$ are the same as defined above.

[8] A process for producing a fluorinated compound, which comprises the steps (I) and (II) as defined in any one of [1] to [7], and a step (III) of subjecting the compound (4) to a cleavage reaction to obtain at least one of a compound (5) represented by the following formula (5) and a compound (6) represented by the following formula (6):

$$FC(=O)-R^{AF}-C(=O)F \quad (5)$$

$$(R^{DF})(R^{CF})(R^{BF})C-C(=O)F \quad (6).$$

[9] The process for producing a fluorinated compound according to [8], wherein in the step (II), the fluorination is carried out in the liquid phase containing a fluorination reaction solvent, and the fluorination reaction solvent is at least one member selected from the group consisting of the compound (5) and the compound (6).

[10] A process for producing a fluorinated compound, which comprises the steps (I), (II) and (III) as defined in [8] or [9], a step (IV) of reacting the compound (5) with hexafluoropropylene oxide to obtain a compound (7) represented by the following formula (7), and a step (V) of heat-decomposing the compound (7) to obtain a compound (8) represented by the following formula (8):

$$FC(=O)-CF(CF_3)-O-CF_2-R^{AF}-C(=O)F \quad (7)$$

$$F_2C=CF-O-Q^{AF}-CF=CF_2 \quad (8)$$

wherein
$R^{AF}$: the same as defined above, and
$Q^{AF}$: when the number of carbon atoms of $R^{AF}$ is 1, $Q^{AF}$ is a single bond; when the number of carbon atoms of $R^{AF}$ is at least 2, $Q^{AF}$ is a group of which the number of carbon atoms is less by 1 than $R^{AF}$ and wherein all hydrogen atoms in a saturated bivalent hydrocarbon group or a partially halogenated bivalent hydrocarbon group are substituted by fluorine atoms.

[11] A process for producing a fluorinated compound, which comprises the steps (I), (II) and (III) as defined in [8] or [9], and a step (VI) of reacting the compound (5) with a compound (9) represented by the following formula (9) to obtain a compound (10) represented by the following formula (10):

$$HO-R \quad (9)$$

$$R-OC(=O)-R^{AF}-C(=O)O-R \quad (10)$$

wherein R is a group selected from the group consisting of —CH$_3$, —CH$_2$CH$_3$ and —CH(CH$_3$)$_2$.

[12] A process for producing a fluorinated compound, which comprises the steps (I), (II) and (III) as defined in [8] or [9], a step (IV) of reacting the compound (5) with hexafluoropropylene oxide to obtain a compound (7) represented by the following formula (7), and a step (VII) of heat-decomposing the compound (7), followed by a reaction with R$^1$OH to obtain a compound (11) represented by the following formula (11):

$$FC(=O)-CF(CF_3)-O-CF_2-R^{AF}-C(=O)F \quad (7)$$

$$F_2C=CF-O-R^{AF}-C(=O)OR^1 \quad (11)$$

wherein
$R^{AF}$: the same as defined above, and
$R^1$: a $C_{1-10}$ alkyl group.

[13] A process for producing a fluorinated polymer, which comprises obtaining a compound (8) by the process as defined in [10] and polymerizing the compound (8).

[14] A process for producing a fluorinated polymer, which comprises obtaining a compound (11) by the process as defined in [12] and polymerizing the compound (11).

Advantageous Effects of Invention

According to the process for producing a fluorinated compound of the present invention, in the fluorination reaction of a partially fluorinated ester, the desired perfluorinated compound can be produced in good yield.

DESCRIPTION OF EMBODIMENTS

In the present specification, a compound represented by the formula (1) is mentioned as compound (1). Compounds represented by other formulae are also mentioned in the same manner.

The following definitions of terms are applied throughout the present specification including claims.

In the present specification, an "organic group" is a group essentially having carbon atoms, and a "hydrocarbon group" is a group consisting of carbon atoms and hydrogen atoms.

In the present specification, "halogen" means fluorine, chlorine, bromine or iodine.

In the present specification, "halogenation" means to substitute an atom which is not a halogen atom (for example, a hydrogen atom bonded to a carbon atom) by a halogen atom, to substitute a group bonded to a carbon atom (for example, a hydroxy group bonded to a carbon atom) by a halogen atom, or to add a halogen atom to an atomic group having no halogen atom (for example, an atomic group consisting of two carbon atoms which form a double bond or a triple bond). Further, to substitute a halogen atom by another halogen atom may be referred to also as "halogenation" of the substituted halogen atom (for example, fluorination may sometimes mean to substitute a chlorine atom or the like by a fluorine atom).

In the present specification, a group "to be halogenated" is a group having at least one of an atom, a group and an atomic group to be halogenated by a halogenation reaction.

In the present specification, a "halogenated group" is an organic group which is formed by halogenating an organic group having a group to be halogenated. For example, a halogenated hydrocarbon group is an organic group formed by halogenating a hydrocarbon group.

A "partially halogenated group" is a group which is a halogenated group and which has a group to be halogenated.

A "perhalogenated group" is a group which is a halogenated group and which has no group to be halogenated.

A "fluorinated perhalogenated group" is a perhalogenated group having at least one fluorine atom among halogen atoms.

In the following present specification including claims, a "fluorination reaction" means a fluorination reaction in the step (II) in the present invention.

Similarly, "fluorination" means fluorination in the fluorination reaction in the step (II) in the present invention.

In the following present specification, an organic group "to be fluorinated" means an organic group having at least one of an atom, a group and an atomic group to be fluorinated by the fluorination reaction in the step (II) in the present invention.

In the present specification, a "hetero atom-containing hydrocarbon group" is a hydrocarbon group having a hetero atom which is not converted by a fluorination reaction (for example, an oxygen atom in an alkoxy group or an etheric oxygen atom) or a hydrocarbon group having a hetero atomic group which is not converted by a fluorination reaction (for example, a carbonyl group or a sulfonyl group).

A halogenated (hetero atom-containing hydrocarbon) group is a group which is formed by halogenating a hetero atom-containing hydrocarbon group. A perhalogenated (hetero atom-containing hydrocarbon) group is a halogenated (hetero atom-containing hydrocarbon) group having no group to be halogenated, and a partially halogenated (hetero atom-containing hydrocarbon) group is a halogenated (hetero atom-containing hydrocarbon) group having a group to be halogenated.

The process for producing a fluorinated compound of the present invention has the following step (I) and step (II) and, as a case requires, has the following step (III) to step (VI).

Now, each step will be described.

[Step (I)]

The step (I) is a step of reacting the following compound (1) and the following compound (2) to produce the following compound (3) (wherein the fluorine content is at least 30 mass %).

$$HOCH_2—R^A—CH_2OH \quad (1)$$

$$X^1C(=O)—C(R^B)(R^C)(R^D) \quad (2)$$

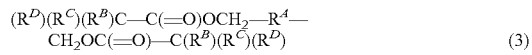

$$(R^D)(R^C)(R^B)C—C(=O)OCH_2—R^A—CH_2OC(=O)—C(R^B)(R^C)(R^D) \quad (3)$$

($R^A$)

$R^A$ is a bivalent saturated hydrocarbon group or a partially halogenated bivalent saturated hydrocarbon group. $R^A$ has no hetero atom such as an etheric oxygen atom. When $R^A$ has no hetero atom such as an etheric oxygen atom, the compound (3) tends not to decompose in the after-mentioned step (II). Thus, the yield of the desired compound (4) in the step (II) is excellent. The number of carbon atoms of $R^A$ is preferably from 1 to 20, particularly preferably from 1 to 10, from the viewpoint of the solubility of the compound (3) in a liquid phase, etc. in the after-mentioned step (II).

The bivalent saturated hydrocarbon group may, for example, be an alkylene group or a bivalent saturated hydrocarbon group having a ring structure. The bivalent saturated hydrocarbon group having a ring structure may, for example, be a bivalent saturated hydrocarbon group having a substituent group selected from the group consisting of a cycloalkyl group, a bicycloalkyl group and a monovalent group having an alicyclic spiro structure; a cycloalkylene group; a bicycloalkylene group; or a bivalent saturated hydrocarbon group having a cycloalkylene group or a bicycloalkylene group as a partial structure.

The bivalent saturated hydrocarbon group is preferably an alkylene group from the viewpoint of the availability. The alkylene group may be linear or branched, and the alkylene group is preferably linear, since the conversion ratio of the compound (3) in the step (II) is excellent.

The partially halogenated bivalent saturated hydrocarbon group is preferably a group wherein some of hydrogen atoms in the above bivalent saturated hydrocarbon group are substituted by halogen atoms, particularly preferably a partially halogenated alkylene group wherein some of hydrogen atoms in an alkylene group are substituted by halogen atoms. The halogen atom in the partially halogenated alkylene group is preferably a fluorine atom, a chlorine atom or a bromine atom.

$R^A$ is preferably a $C_{1-20}$ linear alkylene group, particularly preferably a $C_{1-10}$ linear alkylene group. Specifically, $—(CH_2)_2—$, $—(CH_2)_3—$, $—(CH_2)_4—$ or the like may be mentioned.

($R^B$, $R^C$ and $R^D$)

$R^B$ is the same fluorinated monovalent organic group as $R^{BF}$, a monovalent organic group to be converted to $R^{BF}$ by a fluorination reaction, a hydrogen atom or a halogen atom.

$R^C$ is the same fluorinated monovalent organic group as $R^{CF}$ or a monovalent organic group to be converted to $R^{CF}$ by a fluorination reaction.

$R^D$ is the same fluorinated monovalent organic group as $R^{DF}$ or a monovalent organic group to be converted to $R^{DF}$ by a fluorination reaction.

In the formula (2), the $—C(R^B)(R^C)(R^D)$ group is a branched group. The branched group has a high bulk, and thereby, the compound (3) having such a group is hardly decomposed in the step (II). Accordingly, the yield of the compound (4) in the step (II) is excellent.

<$R^B$>

When $R^B$ is the same fluorinated monovalent organic group as $R^{BF}$, $R^B$ is a fluorinated monovalent organic group which is not fluorinated by a fluorination reaction. For example, a fluorinated perhalogenated monovalent saturated hydrocarbon group; a fluorinated perhalogenated (hetero atom-containing monovalent saturated hydrocarbon) group; etc. may be mentioned.

The organic group to be fluorinated by the fluorination reaction in the step (II) has at least one member selected from the group consisting of the following atom, atomic group and group. The organic group which is not fluorinated by the fluorination reaction does not have any one of them.

The atom to be fluorinated by the fluorination reaction may, for example, be a hydrogen atom bonded to a carbon atom.

The atomic group to be fluorinated by the fluorination reaction may, for example, be an atomic group to which a fluorine atom can be added, such as $>C=C<$ or $—C\equiv C—$. $>C=C<$ is fluorinated to $>CF—CF<$, and $—C\equiv C—$ is fluorinated to $—CF_2—CF_2—$. Further, an atom to be fluorinated may be bonded to the atomic group to be fluorinated, and for example, $—CH=CH—$ is fluorinated to $—CF_2—CF_2—$.

The group to be fluorinated by the fluorination reaction may, for example, be a carboxy group to become a fluorocarbonyl group by a fluorination reaction; or a group having a carbonyl group inserted between a carbon-carbon bond of an alkyl group.

The monovalent saturated hydrocarbon group to become a fluorinated perhalogenated monovalent saturated hydrocarbon group or a fluorinated perhalogenated (hetero atom-containing monovalent saturated hydrocarbon) group may, for example, be an alkyl group, a cycloalkyl group or a monovalent saturated hydrocarbon group having a ring structure (such as a cycloalkyl group, a cycloalkylalkyl group or a bicycloalkyl group, a group having an alicyclic Spiro structure or a group having such a group as a partial structure).

When $R^B$ is the same fluorinated monovalent organic group as $R^{BF}$, specifically $R^B$ is preferably a fluorinated perhalogenated alkyl group, a fluorinated perhalogenated alkyl group having at least one etheric oxygen atom, a fluorinated perhalogenated alkoxy group or a fluorinated perhalogenated alkoxy group having at least one etheric oxygen atom, particularly preferably a perfluoroalkyl group, a perfluoroalkyl group having at least one etheric oxygen atom, a perfluoroalkoxy group or a perfluoroalkoxy group having at least one etheric oxygen atom.

When $R^B$ is the same fluorinated monovalent organic group as $R^{BF}$, the number of carbon atoms of $R^B$ is preferably from 1 to 20, particularly preferably from 1 to 10, from the viewpoint of the solubility of the compound (3) in the liquid phase in the after-mentioned step (II), suppressing the decomposition of the compound (3) in the step (II), etc. $R^B$ may be linear or branched.

When $R^B$ is a monovalent organic group to become $R^{BF}$ by a fluorination reaction, $R^B$ may, for example, be a monovalent saturated hydrocarbon group; a hetero atom-containing monovalent saturated hydrocarbon group; a partially halogenated monovalent saturated hydrocarbon group; a partially halogenated (hetero atom-containing monovalent saturated hydrocarbon) group; a monovalent unsaturated hydrocarbon group; a hetero atom-containing monovalent unsaturated hydrocarbon group; a partially halogenated monovalent unsaturated hydrocarbon group; a partially halogenated (hetero atom-containing monovalent unsaturated hydrocarbon) group; or a monovalent organic group having a group to be fluorinated.

The monovalent saturated hydrocarbon group in the hetero atom-containing monovalent saturated hydrocarbon group, the partially halogenated monovalent saturated hydrocarbon group and the partially halogenated (hetero atom-containing monovalent saturated hydrocarbon) group may, for example, be the same group exemplified as the monovalent saturated hydrocarbon group in the fluorinated perhalogenated monovalent saturated hydrocarbon group and the fluorinated perhalogenated (hetero atom-containing monovalent saturated hydrocarbon) group.

Specifically, the monovalent unsaturated hydrocarbon to be fluorinated may, for example, be a cyclohexenyl group, a phenyl group, an alkenyl group or an alkynyl group.

When $R^B$ is the monovalent organic group to be converted to $R^{BF}$ by a fluorination reaction, $R^B$ is particularly preferably a monovalent saturated hydrocarbon group; a hetero atom-containing monovalent saturated hydrocarbon group; a partially halogenated monovalent saturated hydrocarbon group; or a partially halogenated (hetero atom-containing monovalent saturated hydrocarbon) group. Specifically, preferred is an alkyl group, an alkoxy group, an alkyl group having at least one etheric oxygen atom, an alkoxy group having at least one etheric oxygen atom, a partially halogenated alkyl group, a partially halogenated alkoxy group, a partially halogenated alkyl group having at least one etheric oxygen atom or a partially halogenated alkoxy group having at least one etheric oxygen atom.

When $R^B$ is the monovalent organic group to be converted to $R^{BF}$ by a fluorination reaction, the number of carbon atoms of $R^B$ is preferably from 1 to 20, particularly preferably from 1 to 10, from the viewpoint of the solubility of the compound (3) in a liquid phase in the after-mentioned step (II), suppressing the decomposition of the compound (3) in the step (II), etc. $R^B$ may be linear or branched.

When $R^B$ is the halogen atom, $R^B$ is preferably a fluorine atom, a chlorine atom or a bromine atom, particularly preferably a fluorine atom.

<$R^C$>

When $R^C$ is the same fluorinated monovalent organic group as $R^{CF}$, $R^C$ may, for example, be the same group as exemplified as $R^B$, and the same group is preferred.

When $R^C$ is a monovalent organic group to be converted to $R^{CF}$ by a fluorination reaction, $R^C$ may, for example, be the same group as exemplified as $R^B$, and the same group is preferred.

When $R^C$ is the same fluorinated monovalent organic group as $R^{CF}$ or a monovalent organic group to be converted to $R^{CF}$ by a fluorination reaction, the number of carbon atoms of $R^C$ is preferably from 1 to 20, particularly preferably from 1 to 10, from the viewpoint of the solubility of the compound (3) in a liquid phase in the after-mentioned step (II), suppressing the decomposition of the compound (3) in the step (II), etc. $R^C$ may be linear or branched.

<$R^D$>

When $R^D$ is the same fluorinated monovalent organic group as $R^{DF}$, $R^D$ may, for example, be the same group as exemplified as $R^B$, and the same group is preferred.

When $R^D$ is a monovalent organic group to be converted to $R^{DF}$ by a fluorination reaction, $R^D$ may, for example, be the same group as exemplified as $R^B$, and the same group is preferred.

When $R^D$ is the same fluorinated monovalent organic group as $R^{DF}$ or a monovalent organic group to be converted to $R^{DF}$ by a fluorination reaction, the number of carbon atoms of $R^D$ is preferably from 1 to 20, particularly preferably from 1 to 10, from the viewpoint of the solubility of the compound (3) in a liquid phase in the after-mentioned step (II), suppressing the decomposition of the compound (3) in the step (II), etc. $R^C$ may be linear or branched.

<Combination of $R^B$, $R^C$ and $R^D$>

As the combination of $R^B$, $R^C$ and $R^D$, a preferred combination is such that either one of $R^C$ and $R^D$ is a $C_{1-3}$ monovalent organic group, either one of $R^C$ and $R^D$ is a $C_{1-10}$ monovalent organic group, and $R^B$ is a hydrogen atom or a halogen atom, from the viewpoint of the solubility of the compound (3) in a liquid phase in the step (II), suppressing the decomposition of the compound (3) in the step (II), etc.

As such a combination, for example, a combination may be mentioned such that $R^C$ is one selected from the group consisting of —$CF_3$, —$CF_2CF_3$, —$CF_2CF_2CF_3$, and —$CF(CF_3)_2$, $R^D$ is one selected from the group consisting of —$CF_3$, —$OCF_2CF(CF_3)OCF_2CF_2CF_3$, —$OCF_3$, —$OCF_2CF_3$, —$OCF_2CF_2CF_3$, —$OCF_2CF_2CFClCF_2Cl$, —$OCF_2CF_2Br$, —$OCF(CF_3)CF_2CFClCF_2Cl$ and —$OCH_2CH_2CH_3$, and $R^B$ is a hydrogen atom or a halogen atom.

As the combination of $R^B$, $R^C$ and $R^D$, the combination is more preferably such that $R^C$ is a $C_{1-3}$ perfluoroalkyl group or a $C_{1-3}$ perfluoroalkoxy group, $R^D$ is a $C_1$ perfluoroalkyl group, a $C_{2-10}$ perfluoroalkyl group having at least one etheric oxygen atom, a $C_{1-10}$ perfluoroalkoxy group or a $C_{2-10}$ perfluoroalkoxy group having at least one etheric oxygen atom, and $R^B$ is a fluorine atom.

The combination of $R^B$, $R^C$ and $R^D$ is particularly preferably a combination such that $R^C$ is a $C_{1-3}$ perfluoroalkyl group, $R^D$ is a $C_1$ perfluoroalkyl group, a $C_{2-6}$ perfluoroalkoxy group or a $C_{4-8}$ perfluoroalkoxy group having at least one etheric oxygen atom, and $R^B$ is a fluorine atom.

A more preferred or particularly preferred combination may, for example, be a combination such that $R^C$ is one selected from the group consisting of —$CF_3$, —$CF_2CF_3$, —$CF_2CF_2CF_3$ and —$CF(CF_3)_2$, $R^D$ is one selected from the group consisting of —$CF_3$, —$OCF_2CF(CF_3)OCF_2CF_2CF_3$ and —$OCF_2CF_2CF_3$, and $R^B$ is a fluorine atom.

($X^1$)

$X^1$ is a halogen atom. As the halogen atom, a fluorine atom, a chlorine atom, a bromine atom or an iodine atom may be mentioned. The halogen atom is preferably a fluorine atom, a chlorine atom or a bromine atom, particularly preferably a fluorine atom, from the viewpoint of the reactivity in the step (1).

(Compound (1))

As the compound (1), specifically the following compound (1-1) may be mentioned.

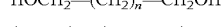

$$HOCH_2-(CH_2)_n-CH_2OH \quad (1\text{-}1)$$

wherein n is the number of carbon atoms of $R^A$ and is preferably from 1 to 20, more preferably from 1 to 10, further preferably from 1 to 8, particularly preferably from 2 to 8.

(Compound (2))

As the compound (2), specifically, the following compounds (2-1) to (2-7) may be mentioned, and the compounds (2-1) to (2-3) are particularly preferred.

$$(CF_3)_2CFC(=O)F \qquad (2\text{-}1)$$

$$CF_3CF_2CF_2OCF(CF_3)CF_2OCF(CF_3)C(=O)F \qquad (2\text{-}2)$$

$$CF_3CF_2CF_2OCF(CF_3)C(=O)F \qquad (2\text{-}3)$$

$$CF_2ClCFClCF_2CF_2OCF(CF_3)C(=O)F \qquad (2\text{-}4)$$

$$CF_2BrCF_2OCF(CF_3)C(=O)F \qquad (2\text{-}5)$$

$$CF_2ClCFClCF_2CF(CF_3)OCF(CF_3)C(=O)F \qquad (2\text{-}6)$$

$$CH_3CH_2CH_2OCF(CF_3)C(=O)F \qquad (2\text{-}7)$$

The boiling point of the compound (2) is preferably from −10 to 200° C., particularly preferably from 0 to 170° C. When the boiling point of the compound (2) falls within the above range, the recovery operation for recovering unreacted compound (2) after the step (I) is easily carried out. For example, when the boiling point of the compound (2) is at least the lower limit in the above range, without a large facility such as a refrigerator, unreacted compound (2) can be recovered. When the boiling point is at most the upper limit in the above range, without a specific heating apparatus, unreacted compound (2) can be recovered by using a general-purpose heating apparatus such as a steamer. The boiling points of the compound (2-1) to (2-7) are from 0 to 170° C. respectively.

The compound (2) can be obtained by a method of obtaining a commercially available product, a method of synthesizing by a known method or the like.

(Combination of the Compound (1) and the Compound (2))

The compound (1) and the compound (2) are combined so that the fluorine content of the compound (3) to be obtained in the step (I) will be at least 30 mass %. When the fluorine content of the compound (3) is at least 30 mass %, the solubility of the compound (3) in a liquid phase in the step (II) is excellent. Thus, the fluorination reaction in the step (II) can be easily carried out in a uniform system, and the yield of the compound (4) in the step (II) is improved. The fluorine content of the compound (3) is preferably from 30 to 86 mass %, particularly preferably from 30 to 76 mass %.

Here, the fluorine content is a mass proportion of fluorine atoms in the molecular weight of the compound.

As the combination of the compound (1) and the compound (2), it is preferred that a compound having no fluorine atom is used as an either one, and a compound having fluorine atoms is used as the other, from the viewpoint of the easiness of the availability of the compound (1) and the compound (2). Among them, it is particularly preferred that a compound having no fluorine atom is used as the compound (1), and a compound having fluorine atoms is used as the compound (2).

(Compound (3))

The compound (3) is preferably a compound having, as an atom, an atomic group or a group to be fluorinated, only a hydrogen atom bonded to a carbon atom. In such a case, the fluorination reaction in the step (II) is only a reaction that a hydrogen atom bonded to a carbon atom is substituted by a fluorine atom. When $-CH_2-R^A-CH_2-$ has, as an atom, an atomic group or a group to be fluorinated, only a hydrogen atom bonded to a carbon atom and each of $R^B$, $R^C$ and $R^D$ is not a group or an atom to be fluorinated, the fluorination of the compound (3) is only a reaction that a hydrogen atom in $-CH_2-R^A-CH_2-$ is substituted by a fluorine atom.

Specifically, as the compound (3), the following compound (3-1) obtained by reacting the compound (1-1) and the compound (2-1), the following compound (3-2) obtained by reacting the compound (1-1) and the compound (2-2), the following compound (3-3) obtained by reacting the compound (1-1) and the compound (2-3), the following compound (3-4) obtained by reacting the compound (1-1) and the compound (2-4), the following compound (3-5) obtained by reacting the compound (1-1) and the compound (2-5), the following compound (3-6) obtained by reacting the compound (1-1) and the compound (2-6), or the following compound (3-7) obtained by reacting the compound (1-1) and the compound (2-7) may be mentioned.

$$(CF_3)_2CFCOOCH_2-(CH_2)_n-CH_2OCOCF(CF_3)_2 \qquad (3\text{-}1)$$

$$CF_3CF_2CF_2OCF(CF_3)CF_2OCF(CF_3)COOCH_2-\\(CH_2)_n-CH_2OCOCF(CF_3)OCF_2CF(CF_3)\\OCF_2CF_2CF_3 \qquad (3\text{-}2)$$

$$CF_3CF_2CF_2OCF(CF_3)COOCH_2-(CH_2)_n-\\CH_2OCOCF(CF_3)OCF_2CF_2CF_3 \qquad (3\text{-}3)$$

$$CF_2ClCFClCF_2CF_2OCF(CF_3)COOCH_2-(CH_2)_n-\\CH_2OCOCF(CF_3)OCF_2CF_2CFClCF_2Cl \qquad (3\text{-}4)$$

$$CF_2BrCF_2OCF(CF_3)COOCH_2-(CH_2)_n-\\CH_2OCOCF(CF_3)OCF_2CF_2Br \qquad (3\text{-}5)$$

$$CF_2ClCFClCF_2CF(CF_3)OCF(CF_3)COOCH_2-\\(CH_2)_n-CH_2OCOCF(CF_3)OCF(CF_3)\\CF_2CFClCF_2Cl \qquad (3\text{-}6)$$

$$CH_3CH_2CH_2OCF(CF_3)COOCH_2-(CH_2)_n-\\CH_2OCOCF(CF_3)OCH_2CH_2CH_3 \qquad (3\text{-}7)$$

In the formulae, n is the same as n in the formula (1-1).

(Reaction of the Compound (1) and Compound (2))

The reaction of the compound (1) and the compound (2) is an esterification reaction and can be carried out by a known method. The esterification reaction can be carried out in the presence of a solvent (hereinafter, referred to also as "esterification reaction solvent") or in the absence of the solvent. The esterification reaction solvent is preferably dichloromethane, chloroform, triethylamine or a mixed solvent of triethylamine and tetrahydrofuran. The amount of the esterification reaction solvent to be used is preferably from 50 to 500 parts by mass, per 100 parts by mass of the total of the compound (1) and the compound (2). In a case where the esterification reaction is carried out in a batch type reactor, the esterification reaction is preferably carried out in the absence of the esterification reaction solvent from the viewpoint of improving the charged amount of the compound (1) and the compound (2) per the unit volume of the reactor and excellent productivity.

In the esterification reaction, the amount of the compound (2) per the compound (1) is preferably from 1.5 to 10 times by mole, particularly preferably from 2 to 5 times by mole.

The lower limit of the temperature for the reaction of the compound (1) and the compound (2) is preferably −50° C. In a case where the reaction is carried out in the presence of an esterification reaction solvent, the upper limit is preferably a lower temperature between 100° C. and the boiling point of the esterification reaction solvent. In a case where the reaction is carried out in the absence of an esterification reaction solvent, the upper limit is preferably 100° C. The reaction temperature is particularly preferably from −50 to 100° C.

The time for the reaction of the compound (1) and the compound (2) can be appropriately changed depending on the rate of supplying starting materials and the amount of compounds used for the reaction. The reaction pressure is preferably from 0 to 2 MPa (gauge pressure).

An acid represented by $HX^1$ is formed by the reaction of the compound (1) and the compound (2). When $X^1$ is a fluorine atom, HF is formed, and therefore it is preferred to let an HF scavenger be present in the reaction system. The HF scavenger may, for example, be an alkali metal fluoride or a trialkylamine. The alkali metal fluoride is preferably NaF or KF. In a case where the HF scavenger is not used, it is preferred that the reaction is carried out at a reaction temperature where HF vaporizes, and HF is exhausted with nitrogen stream. The amount of the HF scavenger is preferably from 1 to 10 times by mole to the compound (2).

A crude product containing the compound (3) formed by the reaction of the compound (1) and the compound (2) may be purified or may be used as it is for the reaction in the step (II). The crude product is preferably purified from the viewpoint of smoothly carrying out the fluorination reaction in the step (II).

The purification method may, for example, be a method of distilling the crude product as it is, a method of treating the crude product with a diluted alkaline water or the like followed by liquid-liquid extraction, a method of extracting the crude product with an appropriate organic solvent followed by distillation or silica gel column chromatography.

[Step (II)]

The step (II) is a step of fluorinating the compound (3) in a liquid phase to obtain a compound (4) represented by the following formula (4). The compound (4) is a compound wherein all of the atom, the atomic group and the group to be fluorinated in the compound (3) are fluorinated. The compound (3) obtained by reacting the compound (1) and the compound (2) is hardly decomposed in the step (II). Thus, by using the compound (3) as a material for fluorination, the compound (4) can be obtained in good yield.

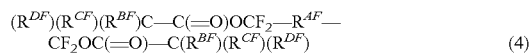

(4)

($R^{AF}$)

$R^{AF}$ is a group wherein all hydrogen atoms in $R^A$ are substituted by fluorine atoms.

($R^{BF}$, $R^{CF}$ and $R^{DF}$)

When $R^B$ is a hydrogen atom, $R^{BF}$ is a fluorine atom, and when $R^B$ is a halogen atom, $R^{BF}$ is the same halogen atom as $R^B$. When $R^B$ is neither a hydrogen atom nor a halogen atom, $R^{BF}$ is a fluorinated monovalent organic group which is the same as or different from $R^B$, and when different, $R^{BF}$ is a group which is $R^B$ fluorinated (group wherein all of the atom, the atomic group and the group to be fluorinated in $R^B$ are fluorinated).

$R^{CF}$ is a fluorinated monovalent organic group which is the same as or different from $R^C$, and when different, $R^{CF}$ is a group which is $R^C$ fluorinated (group wherein all of the atom, the atomic group and the group to be fluorinated in $R^C$ are fluorinated).

$R^{DF}$ is a fluorinated monovalent organic group which is the same as or different from $R^D$, and when different, $R^{DF}$ is a group which is $R^D$ fluorinated (group wherein all of the atom, the atomic group and the group to be fluorinated in $R^D$ are fluorinated).

(Compound (4))

Specifically, as the compound (4), the following compound (4-1) obtained by the fluorination reaction of the compound (3-1), the following compound (4-2) obtained by the fluorination reaction of the compound (3-2), the following compound (4-3) obtained by the fluorination reaction of the compound (3-3), the following compound (4-4) obtained by the fluorination reaction of the compound (3-4), the following compound (4-5) obtained by the fluorination reaction of the compound (3-5), the following compound (4-6) obtained by the fluorination reaction of the compound (3-6) or the following compound (4-7) obtained by the fluorination reaction of the compound (3-7), may be mentioned.

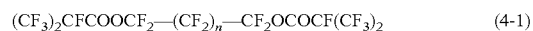 (4-1)

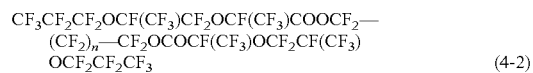 (4-2)

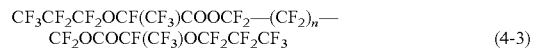 (4-3)

 (4-4)

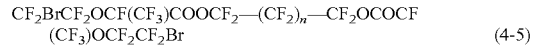 (4-5)

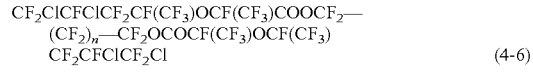 (4-6)

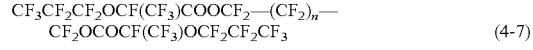 (4-7)

In the formulae, n is the same as n in the formula (1-1).

(Fluorination Reaction of Compound (3))

The fluorination reaction of the compound (3) is carried out in a liquid phase. The fluorination reaction is preferably carried out in a liquid phase containing a solvent (hereinafter referred to as also "fluorination reaction solvent"). As the fluorine source, fluorine gas is preferably used. As the fluorine gas, fluorine gas diluted with inert gas is preferably used. As the inert gas, a noble gas such as helium gas, neon gas or argon gas or nitrogen gas may be mentioned, nitrogen gas or helium gas is preferred, and from the viewpoint of economic advantage, nitrogen gas is particularly preferred. The proportion of the fluorine gas (hereinafter referred to as also "fluorine gas amount") is preferably from 30 to 60 vol % in 100 vol % of the total of fluorine gas and inert gas. When the fluorine gas amount is at least the lower limit in the above range, a predetermined amount of fluorine gas required for a fluorination reaction can be supplied to a reactor for a short time, and thereby the productivity is excellent. Further, the conversion rate of the compound (3) is high, the selectivity of the compound (4) is made to be high. When the fluorine gas amount is at most the upper limit in the above range, the safety is excellent.

The compound (3) obtained by reacting the compound (1) and the compound (2) has a high conversion rate of the compound (3) and a high selectivity of the compound (4) even under a condition that the fluorine gas amount is relatively high. Thus, under such conditions that the fluorine gas amount is high, and the productivity is excellent, the compound (4) can be obtained in good yield.

The fluorination reaction solvent is preferably a fluorinated solvent which is not fluorinated by a fluorination reaction and may, for example, be a perfluoroalkane or an organic solvent prepared by perfluorinating a known organic solvent having at least one atom selected from the group consisting of a chlorine atom, a nitrogen atom and an oxygen atom in its structure.

The fluorination reaction solvent is preferably a solvent being liquid at from −100 to 300° C., particularly preferably a solvent being liquid at from −80 to 200° C.

As the fluorination reaction solvent, a solvent in which the solubility of the compound (3) is high is preferably used, a fluorinated solvent in which at least 1 mass % of the compound (3) is dissolved at 20° C. is particularly preferred, and a solvent in which at least 5 mass % of the compound (3) is dissolved is particularly preferred.

As the fluorination reaction solvent, specifically, perfluoroalkanes (tradename: FC-72, etc.), perfluoroethers (tradename: FC-75, FC-77, etc.), perfluoropolyethers (tradename: KRYTOX, FOMBLIN, GALDEN, DEMNUM, etc.), chlorofluoroethers, chlorofluorocarbons (tradename: FLON LUBE), chlorofluoropolyethers, perfluoroalkylamines (for example, perfluorotrialkylamine, etc.), and an inert fluid (tradename: FLUORINERT) may be mentioned.

The fluorination reaction solvent is preferably a fluorinated solvent having an etheric oxygen atom, and for example, the above mentioned perfluoroethers, perfluoropolyethers and chlorofluoroethers may be mentioned. Among them, a fluorinated solvent having no chlorine atom is preferred, and a perfluoroether or a perfluoropolyether is particularly preferred.

As the fluorination reaction solvent, it is also preferred to use at least one member of the compound (5) and the compound (6) which are products in the after-mentioned step (III). When at least one member of the compound (5) and the compound (6) is used, it is not necessary to recover the solvent after the step (III), and thereby the post treatment is simple. In usual, the fluorination reaction solvent is preferably the compound (6), since the compound (5) is a desired product.

The amount of the fluorination reaction solvent to be used is preferably at least 5 times by mass, particularly preferably from 10 to 100 times by mass, to the compound (3).

The reaction system for the fluorination reaction is preferably a batch system or a continuous system. The fluorination reaction is preferably carried out by the <Method 1> or the <Method 2> which will be described hereinafter, and the fluorination reaction is particularly preferably the <Method 2> from the viewpoint of the reaction yield and the selectivity of the compound (4). Further, the fluorine gas is preferably diluted with an inert gas such as nitrogen gas for use, whether the reaction is carried out by a batch system or by a continuous system.

<Method 1>

A method wherein the compound (3) and a fluorination reaction solvent are charged into a reactor, stirring is initiated, and the reaction is carried out while continuously supplying fluorine gas diluted with an inert gas to the fluorination reaction solvent at a prescribed reaction temperature and reaction pressure.

<Method 2>

A method wherein a fluorination reaction solvent is charged into a reactor and stirred. Then, the fluorine gas diluted with an inert gas, the compound (3) and the fluorination reaction solvent are continuously supplied to the fluorination reaction solvent in a prescribed molar ratio, under prescribed reaction temperature and reaction pressure.

<Method 3>

A fluorination reaction solvent is continuously charged into a tubular reactor and flown in the tubular reactor. Then, fluorinated gas diluted with inert gas and a fluorination reaction solvent in which the compound (3) is dissolved are continuously supplied respectively into the stream of the fluorination reaction solvent in the tubular reactor at proportions such that the fluorine gas and the compound (3) will be the predetermined molar ratio, and they are mixed. In the tubular reactor, the fluorine gas and the compound (3) are contacted and reacted, and the fluorination reaction solvent containing a reaction product is removed from the tubular reactor. In this method, the fluorination reaction solvent is circulated, and the reaction product is removed from the circulating fluorination reaction solvent, whereby the fluorination reaction can be carried out by the continuous method.

Similarly to the method 3, in the method 2, at the time of supplying the compound (3), the compound (3) diluted with a fluorination reaction solvent is preferably supplied, whereby the selectivity of the compound (4) is improved, and the amount of byproducts is suppressed. Further, at the time of diluting the compound (3) with the solvent, the amount of the fluorination reaction solvent is preferably at least 5 times by mass, particularly preferably at least 10 times by mass, to the compound (3).

In either a batch system or in a continuous system, in the fluorination reaction, the amount of fluorine ($F_2$) to fluorinate them is preferably adjusted to be always in an excess amount, to all of the atom, the atomic group and the group to be fluorinated in the compound (3). The amount of fluorine is preferably at least 1.1 times by equivalent, particularly preferably at least 1.3 times by equivalent, to the ideal amount required for fluorinating all of the atom, the atomic group and the group to be fluorinated.

For example, in a case where the compound (3) has only atoms to be fluorinated among the atoms, atomic groups and groups to be fluorinated, and the atoms to be fluorinated are hydrogen atoms, the amount of fluorine ($F_2$) is preferably always in an excess amount to the hydrogen atoms. Specifically, the amount of fluorine is preferably at least 1.1 times by equivalent (i.e. at least 1.1 times by mole) to the hydrogen atoms, particularly preferably at least 1.3 times by equivalent (i.e. at least 1.3 times by mole) from the viewpoint of the selectivity. The amount of fluorine is preferably in an excess amount from the beginning to the end of the reaction. Accordingly, when the fluorination reaction solvent is charged to the reactor at the beginning of the reaction, it is preferred that a sufficient amount of fluorine is preliminary dissolved in the fluorination reaction solvent.

The temperature of the liquid phase in the fluorination reaction is preferably from 10 to 50° C., particularly preferably from 10 to 30° C., from the viewpoint of the yield of the compound (4), the selectivity, the safety and easily carrying out industrial experiment.

The reaction pressure in the fluorination reaction is not particularly restricted and is preferably atmospheric pressure to 2 MPa (gauge pressure) from the viewpoint of the yield of the compound (4), the selectivity, the safety and easily carrying out the industrial experiment.

Further, in order to let the fluorination reaction proceed efficiently, it is preferred to add a C—H bond-containing compound other than the compound (3) to the reaction system, or to carry out ultraviolet irradiation. Such is preferably carried out at a later stage of the fluorination reaction, whereby the compound (3) present in the reaction system can efficiently be fluorinated, and the yield of the compound (3) can remarkably be improved.

The C—H bond-containing compound is preferably an aromatic hydrocarbon, and benzene, toluene or the like may be mentioned. The amount of the C—H bond-containing compound to be added is preferably from 0.1 to 10 mol %, particularly preferably from 0.1 to 5 mol %, to the hydrogen atoms in the compound (3).

The C—H bond-containing compound is preferably added to the reaction system wherein fluorine gas is present. Further, in a case where the C—H bond-containing compound is added, it is preferred to pressurize the reaction system. The pressure for pressurizing is preferably from 0.01 to 5 MPa (gauge pressure).

In a case where ultraviolet ray is applied, the time for ultraviolet irradiation is preferably from 0.1 to 3 hours.

In the fluorination reaction in which a hydrogen atom bonded to a carbon atom is substituted by a fluorine atom, HF is formed as a byproduct. To remove the byproduct HF, it is preferred to use a HF scavenger. Specifically, a method to let a HF scavenger coexist in the reaction system or a method to let the discharge gas contact with a HF scavenger at the gas outlet of the reactor, may be mentioned. As such a HF scavenger, the same ones as mentioned above may be employed, and NaF is preferred.

In a case where an HF scavenger is permitted to coexist in the reaction system, the amount of the HF scavenger is preferably from 1 to 20 times by mole, particularly preferably from 1 to 5 times by mole to hydrogen atoms present in the compound (3). In the case where the HF scavenger is placed at the gas outlet of the reactor, it is preferred to use a packed layer of NaF pellets which is formed by molding NaF as the HF scavenger into pellets and packing the NaF pellets. Specifically, it is preferred to arrange (a) a cooler (preferably to maintain the temperature at from 10° C. to room temperature, particularly preferably at about 20° C.), (b) a packed layer of NaF pellets and (c) a cooler (preferably to maintain the temperature from −78° C. to +10° C., more preferably from −30° C. to 0° C.) in series in the order of (a)-(b)-(c). Further, the cooler (c) may be provided with a liquid returning line to return the condensed liquid from the cooler (c) to the reactor.

The crude product containing the compound (4) obtained by the fluorination reaction, may be used directly for the subsequent step, or may be purified to one having a high purity. The purification method may, for example, be a method wherein the crude product is distilled directly under atmospheric pressure or reduced pressure.

[Step (III)]

The step (III) is a step of subjecting the compound (4) to a cleavage reaction to obtain at least one member of the compound (5) represented by the following formula (5) and the compound (6) represented by the following formula (6).

$$FC(=O)—R^{AF}—C(=O)F \quad (5)$$

$$(R^{DF})(R^{CF})(R^{BF})C—C(=O)F \quad (6)$$

(Compound (5))

As the compound (5), the following compound (5-1) obtained by subjecting the compound (4-1) to (4-7) to a cleavage reaction.

$$FC(=O)—(CF_2)_n—C(=O)F \quad (5-1)$$

wherein n is the same as n in the formula (1-1).

(Compound (6))

As the compound (6), the following compound (6-1) obtained by subjecting the compound (4-1) to a cleavage reaction, the following compound (6-2) obtained by subjecting the compound (4-2) to a cleavage reaction, the following compound (6-3) obtained by subjecting the compound (4-3) to a cleavage reaction, the following compound (6-4) obtained by subjecting the compound (4-4) to a cleavage reaction, the following compound (6-5) obtained by subjecting the compound (4-5) to a cleavage reaction, the following compound (6-6) obtained by subjecting the compound (4-6) to a cleavage reaction and the following compound (6-7) obtained by subjecting the compound (4-7) to a cleavage reaction, may be mentioned.

$$(CF_3)_2CFC(=O)F \quad (6-1)$$

$$CF_3CF_2CF_2OCF(CF_3)CF_2OCF(CF_3)C(=O)F \quad (6-2)$$

$$CF_3CF_2CF_2OCF(CF_3)C(=O)F \quad (6-3)$$

$$CF_2ClCFClCF_2CF_2OCF(CF_3)C(=O)F \quad (6-4)$$

$$CF_2BrCF_2OCF(CF_3)C(=O)F \quad (6-5)$$

$$CF_2ClCFClCF_2CF(CF_3)OCF(CF_3)C(=O)F \quad (6-6)$$

$$CF_3CF_2CF_2OCF(CF_3)C(=O)F \quad (6-7)$$

(Cleavage Reaction of Compound (4))

The cleavage reaction of the compound (4) is a dissociation reaction of the ester bond. The dissociation reaction is preferably carried out by a pyrolysis or by a dissociation reaction carried out in the presence of a nucleophilic agent or an electrophilic agent. The dissociation reaction is particularly preferably a dissociation reaction carried out in the presence of a nucleophilic agent or an electrophilic agent.

In a case where the dissociation reaction of an ester bond is carried out by reacting the compound (4) with a nucleophilic agent or an electrophilic agent in a liquid phase, such a reaction may be carried out in the presence or absence of the dissociation reaction solvent. The dissociation reaction is preferably carried out in the absence of the dissociation reaction solvent, since the compound (4) itself serves as a solvent, and it is not required to separate a solvent from the reaction product. As the nucleophilic agent, F⁻ is preferred, and particularly preferred is F⁻ derived from an alkali metal fluoride. As the alkali metal fluoride, NaF, NaHF₂, KF or CsF is preferred, and among them, KF is particularly preferred from the viewpoint of the reactivity.

In a case where the dissociation reaction of the ester bond is carried out by using F⁻ as a nucleophilic agent, F⁻ will be nucleophilically added to the carbonyl group present in the ester bond in the compound (4), whereby —OCF₂—R^{AF}—CF₂O— will be detached, and the compound (6) will be formed. Further, F⁻ will be detached from —OCF₂—R^{AF}—CF₂O— to form the compound (5). The detached F⁻ will react with another molecule of the compound (4) in a similar manner. Accordingly, the nucleophilic agent initially employed for the reaction may be in a catalytic amount or in an excess amount. The amount of the nucleophilic agent such as F⁻ is preferably from 0.1 to 500 mol %, more preferably from 0.1 to 100 mol %, particularly preferably from 0.5 to 50 mol %, based on the compound (4).

The reaction temperature is preferably from −30° C. to the boiling point of the solvent or the compound (4), more preferably from −20° C. to 250° C.

The dissociation reaction is also preferably carried out while conducting distillation by a reaction apparatus having a distillation column.

Further, in the above explained method, in a case where the compound (6) formed in the step (III) is the same compound as the compound (2) used in the step (I), the compound (6) formed in the step (III) is used (recycled) as the compound (2) in the step (I), whereby the compound (5) can be continuously produced. For example, a method may be mentioned such that a part of or all of the formed compound (6) is used as the compound (2) and reacted with the compound (1).

Further, as described above, the compound (6) can be used as a fluorination reaction solvent. Accordingly, the compound (1) is mixed with an excess amount of the compound (6) and reacted to form a compound (3), whereby a solution of the compound (6) in which the compound (3) is dissolved can be formed. This solution can be used as a fluorination reaction solvent in which the compound (3) is dissolved in the step (II).

[Step (IV) and Step (V)]

The step (IV) is a step of reacting the compound (5) and hexafluoropropylene oxide (hereinafter referred to also as "HFPO") to obtain a compound (7) represented by the following formula (7). The step (V) is a step of pyrolyzing the compound (7) to obtain a compound (8) represented by the following formula (8). The compound (8) is a fluorinated monomer to be cyclopolymerized and is useful as a material for a fluorinated resin. When the compound (8) is produced from the compound (5), by employing a production method wherein the compound (7) is formed as an intermediate as described above, the compound (8) can be efficiently produced by a few steps.

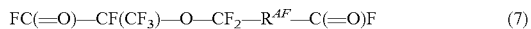

$$FC(=O)-CF(CF_3)-O-CF_2-R^{AF}-C(=O)F \quad (7)$$

$$F_2C=CF-O-Q^{AF}-CF=CF_2 \quad (8)$$

($R^{AF}$)

$R^{AF}$ is the same as the above definition, namely, a group having all hydrogen atoms in $R^A$ substituted by fluorine atoms.

($Q^{AF}$)

$Q^{AF}$: when the number of carbon atoms of $R^{AF}$ is 1, $Q^{AF}$ is a single bond; when the number of carbon atoms of $R^{AF}$ is at least 2, $Q^{AF}$ is a group of which the number of carbon atoms is less by 1 than $R^{AF}$ and wherein all hydrogen atoms in a bivalent saturated hydrocarbon group or a partially halogenated bivalent saturated hydrocarbon group are substituted by fluorine atoms.

(Compound (7))

As the compound (7), the following compound (7-1) obtained by reacting the compound (5-1) and HFPO, may be mentioned.

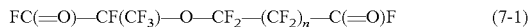

$$FC(=O)-CF(CF_3)-O-CF_2-(CF_2)_n-C(=O)F \quad (7-1)$$

wherein n is the same as n in the formula (1-1).

(Compound (8))

As the compound (8), the following compound (8-1) obtained by pyrolyzing the compound (7-1) may be mentioned.

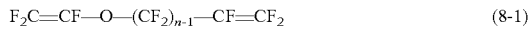

$$F_2C=CF-O-(CF_2)_{n-1}-CF=CF_2 \quad (8-1)$$

wherein n is the same as n in the formula (1-1).

Among them, $F_2C=CF-O-(CF_2)_2-CF=CF_2$ wherein n is 3 and $F_2C=CF-O-CF_2-CF=CF_2$ wherein n is 2 are particularly useful as fluorinated monomers to be cyclopolymerized. As a polymer to be obtained, CYTOP (registered trademark), manufactured by Asahi Glass Company, Limited may be mentioned.

The reaction in which the compound (5) and HFPO are reacted to obtain the compound (7) may be carried out in the presence of or in the absence of a solvent. When the solvent is used, tetraglyme is preferred as the solvent. The reaction temperature is preferably from −50 to 0° C., and particularly preferably from −15 to −5° C. from the viewpoint of easily controlling the reaction and the selectivity of the compound (7). The reaction is preferably carried out under normal pressure and specifically, particularly preferably from −0.1 to 0.5 MPa (gauge pressure). The reaction is carried out in the absence of moisture and acidic components.

The reaction to pyrolyze the compound (7) is preferably carried out in the presence of a catalyst in a gas phase. For example, a method may be mentioned such that by using a fluidized bed reaction apparatus, a reaction is carried out in a reactor in which glass beads are packed as a catalyst. In the case of this method, without temporarily forming a metal salt of the compound (7), the compound (8) can be directly obtained from the compound (7) by one step.

The reaction is preferably carried out under conditions of normal pressure, the reaction temperature of from 100 to 350° C. and the passing time of the compound (7) of from 1 to 30 seconds, from the viewpoint of suppressing of excessively decomposing the compound (7) and isomerization of the compound (7). Here, the passing time is a time during which the compound (7) is in contact with a catalyst packing layer where a catalyst is packed.

[Step (VI)]

The step (VI) is a step of reacting the compound (5) and a compound (9) represented by the following formula (9) to obtain a compound (10) represented by the following formula (10). The compound (10) can be converted to a diisocyanate compound having an $R^{AF}$ group, and the diisocyanate compound having an $R^{AF}$ group is useful as a fluorinated polyurethane resin material, an intermediate for an adhesive for medical use, etc.

$$HO-R \quad (9)$$

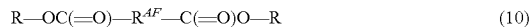

$$R-OC(=O)-R^{AF}-C(=O)O-R \quad (10)$$

(R)

R is a group selected from the group consisting of —$CH_3$, —$CH_2CH_3$ and —$CH(CH_3)_2$.

($R^{AF}$)

$R^{AF}$ is the same as defined above, namely, a group having all hydrogen atoms in $R^A$ substituted by fluorine atoms.

(Compound (9))

The compound (9) is either $CH_3OH$, $CH_3CH_2OH$ or $(CH_3)_2CHOH$.

(Compound (10))

As the compound (10), the following compound obtained by reacting the compound (5-1) and the compound (9) may be mentioned.

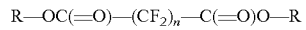

$$R-OC(=O)-(CF_2)_n-C(=O)O-R$$

wherein n is the same as n in the formula (1-1).

The reaction of the compound (5) and the compound (9) may be carried out in the presence or in the absence of a solvent. The solvent is preferably a solvent which has no reactivity with the compound (10) and can be separated from the compound (10) by a method such as distillation separation or column separation. The reaction may be carried out in the absence of a solvent, since the compound (9) itself serves as a solvent. The lower limit of the reaction temperature is preferably −20° C. The upper limit of the reaction temperature is preferably a lower temperature between 100° C. and the boiling point of the solvent. The reaction temperature is particularly preferably from 0 to 40° C. The pressure is preferably from 0 to 2 MPa (gauge pressure).

In the reaction of the compound (5) and the compound (9), HF is formed as a byproduct. To remove the byproduct HF, it is preferred to use an HF scavenger or an alkaline aqueous solution. As the HF scavenger, the above exemplified one may be similarly used. The alkaline aqueous solution may, for example, be a potassium hydroxide aqueous solution or a sodium hydroxide solution. In a case where the HF scavenger is not used, it is preferred to carry out the reaction at a temperature that HF vaporizes, and HF is exhausted with nitrogen stream to the outside of the reaction system. The amount of the HF scavenger or the alkaline aqueous solution to be used is preferably from 1 to 10 times by mole to the compound (5).

[Step (IV) and Step (VII)]

The step (IV) is a step of reacting the compound (5) and HFPO to obtain a compound (7) represented by the following formula (7) as described above. The step (VII) is a step of pyrolyzing the compound (7), followed by reacting with $R^1OH$ to obtain a compound (11) represented by the following formula (11). The compound (11) is useful as a material for a fluorinated resin. In a case where the compound (11) is produced from the compound (5), by employing the production method in which the compound (7) is formed as an intermediate as described above, the compound (11) can be efficiently obtained by a few steps.

$$FC(=O)-CF(CF_3)-O-CF_2-R^{AF}-C(=O)F \qquad (7)$$

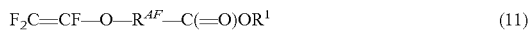
$$F_2C=CF-O-R^{AF}-C(=O)OR^1 \qquad (11)$$

$(R^{AF})$ $R^{AF}$ is the same as defined above, namely, a group having all hydrogen atoms in $R^A$ substituted by fluorine atoms.

$(R^1)$ $R^1$: $C_{1-10}$ alkyl group (Compound (11))

As the compound (11), the following compound (11-1) obtained by pyrolyzing the compound (7-1), followed by reacting with $R^1OH$, may be mentioned.

$$F_2C=CF-O-(CF_2)_n-C(=O)OR^1 \qquad (11-1)$$

wherein n is the same as n in the formula (1-1).

Among them, $F_2C=CF-O-(CF_2)_n-C(=O)OCH_3$ wherein $R^1$ is $CH_3$ (namely $R^1OH$ is methanol) is useful as a fluorinated monomer for producing a fluorinated polymer, and n is particularly preferably 3.

The reaction to pyrolyze the compound (7) for producing the compound (11) is preferably carried out in a gas phase in the presence of a catalyst. For example, a method may be mentioned such that by using a fluidized bed reaction apparatus, the reaction is carried out in a reactor in which glass beads are packed as a catalyst. After passing through a catalyst layer, the compound (7) is reacted with methanol, whereby without temporarily isolating the compound (7), the compound (11) can be directly obtained from the compound (7).

The reaction is preferably carried out under such conditions that under normal pressure, the reaction temperature is from 100 to 350° C., preferably from 150 to 250° C., and the passing time of the compound (7) is from 1 to 20 seconds, from the viewpoint of suppressing excessive decomposition of the compound (7). Further, the passing time is a time during which the compound (7) is in contact with a catalyst packed layer where a catalyst is packed.

As described above, in the production process of the present invention, in the step (II), the compound (1) obtained in the step (I) and the compound (2) are reacted to obtain the compound (3), and the compound (3) is fluorinated, whereby the compound (4) can be obtained in good yield.

Further, by carrying out the steps (III) to (V), the compound (5) and the compound (6) are obtained from the compound (4), and the compound (8) can be obtained from the compound (5) via the compound (7). The compound (8) is useful as a fluorinated monomer to be cyclopolymerized.

Further, in the step (VI), the compound (10) can be obtained from the compound (5). The compound (10) is useful as an intermediate for a medical adhesive, etc.

Further, in the step (VII), the compound (11) can be obtained from the compound (5). The compound (11) is useful as a fluorinated monomer.

The compound (8) and the compound (11) may be each independently polymerized as a fluorinated monomer to obtain a fluorinated polymer or may be polymerized in combination to obtain a fluorinated polymer.

EXAMPLES

Now, the present invention will be described in further detail with reference to Examples. However, the present invention is by no means thereby restricted. Ex. 1 to 5 and Ex. 11 and 12 are Working Examples of the present invention, and Ex. 6 to 10 are Comparative Examples.

Abbreviations in Ex. mean the followings.

$(HFPO)_3$: $CF_3CF_2CF_2OCF(CF_3)CF_2OCF(CF_3)C(=O)F$

TMS: Tetramethylsilane

[GC Purity]

GC purity is a value (mol %) of the proportion of the compound (3) in the crude liquid, which is determined by the peak area ratio of gas chromatography (GC) and represented by percentage.

[Measurement of $^{19}$F-NMR and $^1$H-NMR]

For the measurement by $^{19}$F-NMR, perfluorobenzene ($C_6F_6$) was used as the internal standard sample, and for the measurement by $^1$H-NMR, TMS was used.

NMR spectrum data are shown within the apparent chemical shift change.

[$^{19}$F-NMR Conversion Ratio]

$^{19}$F-NMR conversion ratio is a value (mol %) of the amount of the converted compound (3) which is represented by percentage of the mol standard in the amount of the compound (3) supplied to the fluorination reaction. $^{19}$F-NMR conversion ratio is obtainable by the formula: 100−(amount of recovered unreacted compound (3)/amount of supplied compound (3))×100.

Specifically, the amount of the compound (3) supplied to the fluorination reaction is an actually measured value, and the amount of the recovered unreacted compound (3) is a value obtained by analyzing a recovered product taken out from the autoclave by $^{19}$F-NMR.

[$^{19}$F-NMR Yield]

$^{19}$F-NMR yield is a value (mol %) of the amount (produced amount) of the recovered compound (4) represented by percentage of the molar standard, per the amount of the compound (3) supplied to the fluorination reaction and obtained by the calculation formula: (amount of recovered compound (4)/amount of supplied compound (3))×100.

Specifically, the amount of the compound (3) supplied to the fluorination reaction is an actually measured value, and the amount of the recovered compound (4) is a value obtained by analyzing a recovered product taken out from the autoclave by $^{19}$F-NMR.

Ex. 1

(Ex. 1-1) Preparation of $(CF_3)_2CFCOO(CH_2)_5OCOCF(CF_3)_2$ (Corresponding to Compound (3-1))

Into a 5 L flask, 1,000 g of $HO(CH_2)_{50}H$ (corresponding to compound (1-1)) was put, and stirred while bubbling nitrogen gas. Then, 4,400 g of $(CF_3)_2CFC(=O)F$ (corresponding to compound (2-1)) was supplied (bubbled) to the liquid phase over 2.5 hours, while maintaining the internal temperature at from 25 to 30° C. of the flask. After the termination of supplying, the mixture was stirred at room temperature for 15 hours, and the obtained crude liquid was recovered.

The GC purity of the crude liquid was 95%.

Further, $^1$H-NMR and $^{19}$F-NMR spectrum were measured, and it was confirmed that the main component was the above-identified compound (fluorine content=53.6 mass %).

NMR Spectrum
$^1$H-NMR (399.78 MHz, solvent: CDCl$_3$, standard: TMS) δ(ppm): 1.42-1.53 (m, 2H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −74.3 (12F), −181.9 (2F).

Ex. 1-2

Preparation of (CF$_3$)$_2$CFCOO(CF$_2$)$_5$OCOCF(CF$_3$)$_2$ (Corresponding to Compound (4-1)

Into a 3,000 mL autoclave made of nickel, 2,800 g of (HFPO)$_3$ was added as a fluorination reaction solvent, stirred and maintained at 25° C. At the gas outlet of the autoclave, a cooler maintained at −20° C. was installed. After supplying nitrogen gas for 1.0 hour, diluted fluorine gas having a fluorine gas amount of 50 vol % which was diluted with nitrogen gas (hereinafter referred to as also "50% fluorine gas") was supplied at 36 L/h for 1 hour.

Then, while supplying 50% fluorine gas at the same flow rate, 40 g of (CF$_3$)$_2$CFCOO(CH$_2$)$_5$OCOCF(CF$_3$)$_2$ obtained in Ex. 1-1 was injected over a period of 2 hours. Further, 50% fluorine gas was supplied at the same flow rate for 1 hour, and further nitrogen gas was supplied for 1 hour.

The formed product in a recovered product from the autoclave contained the above-identified compound as the main product, the $^{19}$F-NMR yield was 96%, and the $^{19}$F-NMR conversation ratio was 98%.

NMR Spectrum:
$^{19}$F-NMR (376.17 MHz, solvent: CDCl$_3$, standard: C$_6$F$_6$) δ(ppm): −74.3 (s, 12F), −86.1 (4F), −122.6 (2F), −125.7 (4F), −181.9 (2F).

[Ex. 2] Preparation of (CF$_3$)$_2$CFCOO(CF$_2$)$_5$OCOCF (CF$_3$)$_2$ (Corresponding to Compound (4-1)

(CF$_3$)$_2$CFCOO(CH$_2$)$_5$OCOCF(CF$_3$)$_2$ was obtained in the same manner as in Ex. 1-1. Then, the experiment was carried out in the same manner as in Ex. 1-2, except that the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

Ex. 3

(Ex. 3-1) Preparation of (CF$_3$)$_2$CFCOO (CH$_2$)$_6$OCOCF(CF$_3$)$_2$ (Corresponding to Compound (3-1)

The experiment was carried out in the same manner as in Ex. 1-1, except that starting materials were changed as shown in Table 1. The GC purity of a recovered crude liquid was 96%. Further, $^1$H-NMR and $^{19}$F-NMR spectrum were measured, and it was confirmed that the main component was the above-identified compound (fluorine content=52.2 mass %).

NMR Spectrum:
$^1$H-NMR (399.78 MHz, solvent: CDCl$_3$, standard: TMS) δ(ppm): 1.42-1.53 (m, 4H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −74.3 (12F), −181.9 (2F).

(Ex. 3-2) Preparation of (CF$_3$)$_2$CFCOO (CF$_2$)$_6$OCOCF(CF$_3$)$_2$ (Corresponding to Compound (4-1)

The experiment was carried out in the same manner as in Ex. 1-2, except that as the compound to be injected in the autoclave, (CF$_3$)$_2$CFCOO(CH$_2$)$_6$OCOCF(CF$_3$)$_2$ obtained in Ex. 3-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: CDCl$_3$, standard: C$_6$F$_6$) δ(ppm): −74.3 (s, 12F), −86.1 (4F), −122.6 (4F), −125.7 (4F)−181.9 (2F).

Ex. 4

(Ex. 4-1) Preparation of CF$_3$CF$_2$CF$_2$OCF(CF$_3$) CF$_2$OCF(CF$_3$)COO(CH$_2$)$_6$—OCOCF(CF$_3$)OCF$_2$CF (CF$_3$)OCF$_2$CF$_2$CF$_3$ (Corresponding to Compound (3-2)

The experiment was carried out in the same manner as in Ex. 1-1, except that starting materials were changed as shown in Table 1. The GC purity of the recovered crude liquid was 97%. Further, $^1$H-NMR and $^{19}$F-NMR spectrum were measured, and it was confirmed that the main component was the above-identified compound (fluorine content=60.1 mass %).

NMR Spectrum:
$^1$H-NMR (399.78 MHz, solvent: CDCl$_3$, standard: TMS) δ(ppm): 1.42-1.53 (m, 4H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −80.9 (4F), −80.5 (6F), −83.1 (16F), −130.7 (4F), −132.7 (2F), −145.2 (2F).

(Ex. 4-2) Preparation of CF$_3$CF$_2$CF$_2$OCF(CF$_3$) CF$_2$OCF(CF$_3$)COO(CF$_2$)$_6$OCOCF(CF$_3$)OCF$_2$CF (CF$_3$)OCF$_2$CF$_2$CF$_3$ (Corresponding to Compound (4-2)

The experiment was carried out in the same manner as in Ex. 1-2, except that as the compound to be injected in the autoclave, CF$_3$CF$_2$CF$_2$OCF(CF$_3$)CF$_2$OCF(CF$_3$)COO (CH$_2$)$_6$OCOCF(CF$_3$)OCF$_2$CF(CF$_3$)OCF$_2$CF$_2$CF$_3$ obtained in Ex. 4-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: CDCl3, standard: C$_6$F$_6$) δ(ppm): −80.9 (4F), −80.5 (6F), −83.1 (16F), −86.1 (4F), −122.6 (4F), −125.7 (4F), −130.7 (4F), −132.7 (2F), −145.2 (2F).

Ex. 5

(Ex. 5-1) Preparation of $CF_3CF_2CF_2OCF(CF_3)CF_2OCF(CF_3)COO(CH_2)_6OCOCF(CF_3)OCF_2CF(CF_3)OCF_2CF_2CF_3$ (Corresponding to Compound (3-2))

The experiment was carried out in the same manner as in Ex. 1-1, except that starting materials were changed as shown in Table 1. The GC purity of the recovered crude liquid was 95%. Further, $^1$H-NMR and $^{19}$F-NMR spectrum were measured, and it was confirmed that the main component was the above-identified compound (fluorine content=60.9 mass %).

NMR Spectrum:
$^1$H-NMR (399.78 MHz, solvent: CDCl$_3$, standard: TMS) δ(ppm): 1.42-1.53 (m, 2H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −80.9 (4F), −80.5 (6F), −83.1 (16F), −130.7 (4F), −132.7 (2F), −145.2 (2F).

(Ex. 5-2) Preparation of $CF_3CF_2CF_2OCF(CF_3)CF_2OCF(CF_3)COO(CF_2)_5OCOCF(CF_3)OCF_2CF(CF_3)OCF_2CF_2CF_3$ (Corresponding to Compound (4-2))

The experiment was carried out in the same manner as in Ex. 1-2, except that as the compound to be injected in the autoclave, $CF_3CF_2CF_2OCF(CF_3)CF_2OCF(CF_3)COO(CH_2)_5OCOCF(CF_3)OCF_2CF(CF_3)OCF_2CF_2CF_3$ obtained in Ex. 5-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: CDCl$_3$, standard: C$_6$F$_6$) δ(ppm): −80.9 (4F), −80.5 (6F), −83.1 (16F), −86.1 (4F), −122.6 (2F), −125.7 (4F), −130.7 (4F), −132.7 (2F), −145.2 (2F).

Ex. 6

(Ex. 6-1) Preparation of $CF_3CF_2CF_2OCF(CF_3)COO(CH_2)_4OCOCF(CF_3)OCF_2CF_2CF_3$ (Corresponding to Compound (3-3))

The experiment was carried out in the same manner as in Ex. 1-1, except that starting materials were changed as shown in Table 1. The GC purity of the recovered crude liquid was 97%. Further, $^1$H-NMR and $^{19}$F-NMR spectrum were measured, and it was confirmed that the main component was the above-identified compound (fluorine content=58.5 mass %).

NMR Spectrum:
$^1$H-NMR (399.78 MHz, solvent: CDCl$_3$, standard: TMS) δ(ppm) 1.70-1.84 (m, 4H), 4.20-4.50 (m, 4H).
$^{19}$F-NMR (376.17 MHz, solvent: CDCl$_3$, standard: C$_6$F$_6$) δ(ppm): −80.5 (6F), −80.9 (4F), −83.1 (6F), −130.7 (4F), −145.2 (2F).

(Ex. 6-2) Preparation of $CF_3CF_2CF_2OCF(CF_3)COO(CF_2)_4OCOCF(CF_3)OCF_2CF_2CF_3$ (Corresponding to Compound (4-3))

The experiment was carried out in the same manner as in Ex. 1-2, except that as the compound to be injected in the autoclave, $CF_3CF_2CF_2OCF(CF_3)COO(CH_2)_4OCOCF(CF_3)OCF_2CF_2CF_3$ obtained in Ex. 6-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: CDCl$_3$, standard: C$_6$F$_6$) δ(ppm): −80.5 (6F), −80.9 (4F), −83.1 (6F), −122.6 (4F), −126.6 (4F)−130.7 (4F), −145.2 (2F).

Ex. 7

(Ex. 7-1) Preparation of $CF_3CF_2COO(CH_2)_5OCOCF_2CF_3$

The experiment was carried out in the same manner as in Ex. 1-1, except that starting materials were changed as shown in Table 1. The GC purity of the recovered crude liquid was 97%. Further, $^1$H-NMR and $^{19}$F-NMR spectrum were measured, and it was confirmed that the main component was the above-identified compound.

NMR Spectrum:
$^1$H-NMR (399.78 MHz, solvent: CDCl$_3$, standard: TMS) δ(ppm): 1.42-1.53 (m, 2H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −83.0 (6F), −121.4 (4F)

(Ex. 7-2) Preparation of $CF_3CF_2COO(CF_2)_5OCOCF_2CF_3$

The experiment was carried out in the same manner as in Ex. 1-2, except that as the compound to be injected in the autoclave, $CF_3CF_2COO(CH_2)_5OCOCF_2CF_3$ obtained in Ex. 7-1 was injected, and the fluorination reaction was carried out under conditions shown in Table 1. However, a combustion reaction occurred, and in a recovered product from the autoclave, many formed products were confirmed. The above-identified compound of the $^{19}$F-NMR yield in the recovered product is shown in Table 1.

NMR Spectrum:
$^{19}$F-NMR (376.17 MHz, solvent: CDCl$_3$, standard: C$_6$F$_6$) δ(ppm): −83.0 (6F), −86.1 (4F), −121.4 (4F), −122.6 (2F), −125.7 (4F).

Ex. 8

(Ex. 8-1) Preparation of $CF_3CF_2COO(CH_2)_6OCOCF_2CF_3$

The experiment was carried out in the same manner as in Ex. 1-1, except that starting materials were changed as shown in Table 1. The GC purity of the recovered crude liquid was 96%. Further, $^1$H-NMR and $^{19}$F-NMR spectrum were measured, and it was confirmed that the main component was the above-identified compound.

NMR Spectrum:
$^1$H-NMR (399.78 MHz, solvent: CDCl$_3$, standard: TMS) δ(ppm): 1.42-1.53 (m, 4H), 1.70-1.84 (m, 4H), 4.20-4.50 (m, 4H).
$^{19}$F-NMR (376.17 MHz, solvent: CDCl$_3$, standard: C$_6$F$_6$) δ(ppm): −83.0 (6F), −121.4 (4F).

(Ex. 8-2) Preparation of $CF_3CF_2COO(CF_2)_6OCOCF_2CF_3$

The experiment was carried out in the same manner as in Ex. 1-2, except that as the compound to be injected in the autoclave, $CF_3CF_2COO(CH_2)_6OCOCF_2CF_3$ obtained in Ex. 8-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: $CDCl_3$, standard: $C_6F_6$) δ(ppm): −83.0 (6F), −86.1 (4F), −121.4 (4F), −122.6 (4F), −125.7 (4F).

Ex. 9

(Ex. 9-1) Preparation of $CF_3CF_2CF_2OCF(CF_3)$
$COOCH_2CH(CH_3)O(CH_2)_5OCOCF(CF_3)$
$OCF_2CF_2CF_3$ The experiment was carried out in the same manner as in Ex. 1-1, except that starting materials were changed as shown in Table 1. The GC purity of the recovered crude liquid was 95%. Further, $^1$H-NMR and $^{19}$F-NMR spectrum were measured, and it was confirmed that the main component was the above-identified compound.

NMR Spectrum:
$^1$H-NMR (399.78 MHz, solvent: $CDCl_3$, standard: TMS) δ(ppm): 1.19 (3H), 1.39-1.49 (2H), 1.54-1.63 (2H), 1.71-1.80 (2H), 3.39-3.53 (2H), 3.66-3.72 (1H), 4.21-4.46 (4H).
$^{19}$F-NMR (376.17 MHz, solvent: $CDCl_3$, standard: $C_6F_6$) δ(ppm): −80.9 (2F), −82.3 (6F), −83.1 (6F), −87.4 (2F), −130.7 (4F), −132.7 (2F).

(Ex. 9-2) Preparation of $CF_3CF_2CF_2OCF(CF_3)$
$COOCF_2CF(CF_3)O(CF_2)_6OCOCF(CF_3)$
$OCF_2CF_2CF_3$ The experiment was carried out in the same manner as in Ex. 1-2, except that as the compound to be injected in the autoclave, $CF_3CF_2CF_2OCF(CF_3)COOCH_2CH(CH_3)O(CH_2)_5OCOCF(CF_3)OCF_2CF_2CF_3$ obtained in Ex. 9-1 was injected, and the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

NMR Spectrum:
$^{19}$F-NMR (376.17 MHz, solvent: $CDCl_3$, standard: $C_6F_6$) δ(ppm): −79.2 to −80.7 (7F), −81.5 to 82.0 (12F), −85.9 to −87 (6F), −122.4 (2F), −125.3 (4F)−129.6 (4F), −131.4 (2F), −144.9 (1F).

[Ex. 10] Preparation of $CF_3CF_2CF_2OCF(CF_3)$
$COOCF_2CF(CF_3)O(CF_2)_5OCOCF(CF_3)$
$OCF_2CF_2CF_3$ $CF_3CF_2CF_2OCF(CF_3)COOCH_2CH(CH_3)O(CH_2)_5$ $OCOCF(CF_3)OCF_2CF_2CF_3$ was obtained in the same manner as in Ex. 9-1. Then, the experiment was carried out in the same manner as in Ex. 9-2, except that the fluorination reaction was carried out under conditions shown in Table 1. The formed product in a recovered product from the autoclave contained the above-identified compound as the main product. The $^{19}$F-NMR yield and the $^{19}$F-NMR conversation ratio are shown in Table 1.

Ex. 11

(Ex. 11-1) Preparation of $CF_3CF_2COO$ $(CH_2)_4OCOCF_2CF_3$

The experiment was carried out in the same manner as in Ex. 1-1, except that starting materials were changed as shown in Table 1. The GC purity of the recovered crude liquid was 98%. Further, $^1$H-NMR and $^{19}$F-NMR spectrum were measured, and it was confirmed that the main component was the above-identified compound.

NMR Spectrum:
$^1$H-NMR (399.78 MHz, solvent: $CDCl_3$, standard: TMS) δ(ppm) 1.70-1.84 (m, 4H), 4.20-4.50 (m, 4H).
$^{19}$F-NMR (376.17 MHz, solvent: $CDCl_3$, standard: $C_6F_6$) δ(ppm): −83.0 (6F), −121.4 (4F).

(Ex. 11-2) Preparation of $CF_3CF_2COO$ $(CF_2)_4OCOCF_2CF_3$

Into a 3,000 mL autoclave made of nickel, 2,800 g of $(HFPO)_3$ was added, stirred and maintained at 25° C. At the outlet of the autoclave, a cooler maintained at −20° C. was installed. Further, a liquid returning line was installed to return a liquid condensed from the cooler maintained at −20° C. to the autoclave. After supplying nitrogen gas for 2 hours, 50% fluorine gas was supplied at a flow rate of 7.8 L/hr for 1 hour. Then, while supplying 50% fluorine gas at the same flow rate, $CF_3CF_2COO(CH_2)_4OCOCF_2CF_3$ (25 g) obtained in Ex. 11-1 was injected over a period of 6 hours. Then, 50% fluorine gas was supplied at the same rate for 1 hour, and further nitrogen gas was supplied for 1 hour. The formed product in a recovered product from the autoclave contained the above-identified compound as the main product, the $^{19}$F-NMR yield was 51%, and the $^{19}$F-NMR conversation ratio was 80%.

Further, while supplying 50% fluorine gas at the same flow rate, $CF_3CF_2COO(CH_2)_4OCOCF_2CF_3$ (25 g) obtained in Ex. 11-1 was injected over a period of 6 hours. Then, 50% fluorine gas was supplied at the same rate for 1 hour, and further nitrogen gas was supplied for 1 hour. The formed product in a recovered product from the autoclave contained the above-identified compound as the main product, the $^{19}$F-NMR yield was 83%, and the $^{19}$F-NMR conversation ratio was 100%.

NMR Spectrum:
$^{19}$F-NMR (376.17 MHz, solvent: $CDCl_3$, standard: $C_6F_6$) δ(ppm): −83.8 (6F), −87.3 (4F), −122.6 (4F), −126.6 (4F)

TABLE 1

| | Starting materials | |
|---|---|---|
| Ex | Compound to be preliminarily added in flask [( ) is mass to be added] | Compound to be added by bubbling [( ) is mass to be added] |
| 1 | HO—$(CH_2)_5$—OH (1,000 g) | $(CF_3)_2CFC(=O)F$ (4,400 g) |

TABLE 1-continued

Starting materials

| Ex | Compound to be preliminarily added in flask [( ) is mass to be added] | Compound to be added by bubbling [( ) is mass to be added] |
|---|---|---|
| 2 | HO—(CH$_2$)$_5$—OH (1,000 g) | (CF$_3$)$_2$CFC(=O)F (4,400 g) |
| 3 | HO—(CH$_2$)$_6$—OH (1,000 g) | (CF$_3$)$_2$CFC(=O)F (3,800 g) |
| 4 | HO—(CH$_2$)$_6$—OH (1,000 g) | CF$_3$CF$_2$CF$_2$OCF(CF$_3$)CF$_2$OCF(CF$_3$)C(=O)F (8,900 g) |
| 5 | HO—(CH$_2$)$_5$—OH (1,000 g) | CF$_3$CF$_2$CF$_2$OCF(CF$_3$)CF$_2$OCF(CF$_3$)C(=O)F (10,000 g) |
| 6 | HO—(CH$_2$)$_4$—OH (1,000 g) | CF$_3$CF$_2$CF$_2$OCF(CF$_3$)COF (7,700 g) |
| 7 | HO—(CH$_2$)$_5$—OH (1,000 g) | CF$_3$CF$_2$C(=O)F (3,400 g) |
| 8 | HO—(CH$_2$)$_6$—OH (1,000 g) | CF$_3$CF$_2$C(=O)F (3,000 g) |
| 9 | HOCH$_2$CH(CH$_3$)O(CH$_2$)$_5$OH (1,000 g) | CF$_3$CF$_2$CF$_2$OCF(CF$_3$)C(=O)F (4,300 g) |
| 10 | HOCH$_2$CH(CH$_3$)O(CH$_2$)$_5$OH (1,000 g) | CF$_3$CF$_2$CF$_2$OCF(CF$_3$)C(=O)F (4,300 g) |
| 11 | HO—(CH$_2$)$_4$—OH (1,000 g) | CF$_3$CF$_2$C(=O)F (3,900 g) |

Fluorination reaction condition

| Ex | Amount of fluorination reaction solvent (g) | Amount of fluorine gas (vol %) | Rate of supplying fluorine gas (L/time) | Time for adding compound to be fluorinated (time) | $^{19}$F-NMR conversion rate (mol %) | $^{19}$F-NMR yield (mol %) |
|---|---|---|---|---|---|---|
| 1 | 2,800 | 50 | 36 | 2 | 98 | 96 |
| 2 | 3,200 | 20 | 30 | 6 | 72 | 66 |
| 3 | 2,800 | 50 | 42 | 2 | 95 | 93 |
| 4 | 2,800 | 50 | 20 | 2 | 100 | 98 |
| 5 | 2,800 | 50 | 17 | 2 | 94 | 93 |
| 6 | 2,800 | 50 | 7.8 | 12 | 100 | 93 |
| 7 | 2,800 | 50 | 45 | 2 | Combustion | 13 |
| 8 | 2,800 | 50 | 52 | 2 | 100 | 62 |
| 9 | 2,800 | 50 | 36 | 2 | 98 | 63 |
| 10 | 2,800 | 20 | 30 | 6 | 88 | 70 |
| 11 | 2,800 | 50 | 7.8 | 6 | 80 | 51 |
|    |       |    |     | 12 | 100 | 83 |

In Ex. 1 to 6, the desired product could be obtained in good yield by the fluorination reaction. Among them, in Ex. 1 and 3 to 6, the desired product could be obtained in good yield under the condition that the amount of fluorine gas was large (50 vol %). On the other hand, in Ex. 7 to 11, the desired product could not be obtained in good yield. For example, in Ex. 7 to 9 where the fluorination reaction was carried out under the condition that the amount of fluorine gas was large, although the conversion ratio was high, the selectivity of the desired product was low, and thereby the yield was low. In Ex. 10 where the fluorination reaction was carried out under the condition that the amount of fluorine gas was small, although the selectivity of the desired product was slightly improved, a sufficient yield could not be obtained. In Ex. 11, the injection time (reaction time) of the compound to be fluorinated was prolonged to improve the conversion ratio, however, the selectivity was low, and a sufficient yield could not be obtained.

Ex. 12

(Ex. 12-1) Preparation of FC(=O)(CF$_2$)$_3$C(=O)F (Corresponding to Compound (5-1)

Into a 1 L flask, 500 g of (CF$_3$)$_2$CFCOO(CF$_2$)$_5$OCOCF(CF$_3$)$_2$ (corresponding to the compound (4-1)) obtained in Ex. 1-2 was charged, and then 4.1 g of a KF powder was charged. While vigorously stirring, the flask was heated at 100° C. for 5 hours in an oil bath. At the upper portion of the flask, a reflux condenser adjusted to a temperature of 20° C. and a gas-collecting fluororesin container were installed in series. After heating, the flask was cooled, and a liquid sample and a gaseous sample were recovered. The liquid sample was purified by distillation. By GC-MS analysis, it was confirmed that the above-identified compound was the main product. The yield was 82 mol %. The yield is mol % of the desired compound contained in a recovered fraction obtained by distillation purification, when the molar number of the desired compound to be theoretically obtained from the charged composition is 100%.

(Ex. 12-2) Preparation of FC(=O)CF(CF$_3$)O(CF$_2$)$_4$C(=O)F (Corresponding to the Compound (7-1)

Into a 2 L autoclave, 360 g of FOC(CF$_2$)$_3$COF obtained in Ex. 12-1, 11.4 g of cesium fluoride and 56.8 g of tetraglyme were charged, and while maintaining the autoclave at −10° C., 260 g of hexafluoropropylene oxide was added. After termination of the reaction, the lower layer was recovered and purified by distillation. By GC-MS, it was confirmed that the above-identified compound was the main product. The yield of the desired compound as defined in Ex. 12-1 was 60 mol %.

(Ex. 12-3) Preparation of $F_2C=CFO(CF_2)_2CF=CF_2$ (Corresponding to the Compound (8-1)

A 1 inch reactor made of Inconel was filled with glass beads so that the filling height would be 20 cm and heated at 330° C. 500 g of $FC(=O)CF(CF_3)O(CF_2)_4C(=O)F$ obtained in Ex. 12-2 was diluted with nitrogen gas so as to be 10 vol % and introduced into the reactor. The linear velocity was controlled at 2.0 cm/s, and while maintaining the passing time of the reaction gas through the glass beads layer to 10 seconds, the reaction was carried out. The reaction outlet gas was collected by means of a dry ice-ethanol trap. The trap-collected liquid was purified by distillation and analyzed by GC-MS, and as a result, it was confirmed that the above-identified compound was the main product. The yield of the desired compound as defined in Ex. 12-1 was 48 mol %.

(Ex. 12-4) Preparation of $F_2C=CFO(CF_2)_2CF=CF_2$ (corresponding to the compound (8-1)

Into a 1 L separable flask, 150 g of $F_2C=CFO(CF_2)_2CF=CF_2$ obtained in Ex. 12-3, 28.0 g of methanol, 3.8 g of an initiator (10 mass % 1,1,1,2,2,3,3,4,4,5,5,6,6-tridecafluorohexane solution of $[(CH_3)_2CHOCO]_2)$, 5.7 g of a dispersing agent (tradename: Newcol 714SN, manufactured by NIPPON NYUKAZAI CO., LTD) and 800 g of ultrapure water were charged, and suspension polymerization was carried out by stirring for the total 26 hours: 20 hours at 40° C. and 6 hours at 50° C. The yield of the obtained polymer particles (cyclopolymer) was 88%, and the intrinsic viscosity was 0.34. The cyclopolymer was a transparent tough polymer and could be dissolved in a perfluorosolvent such as a perfluorotributylamine to form a thin coating film on a silicon wafer or glass.

The yield of the polymer particles is mass % of the obtained polymer particles, when the mass of charged monomers is 100%.

The intrinsic viscosity is defined by the following formula (A). The intrinsic viscosity was measured as described below. A solution was prepared by dissolving polymer particles in 1,1,1,2,2,3,4,5,5,5-decafluoro-3-methoxy-4-(trifluoromethyl)-pentane, and while diluting the concentration c, its flowing velocity was measured by means of an Ubbelohde viscometer. The intrinsic viscosity is an extrapolated value obtained by double logarithmic plotting ηsp/c and c and extrapolating its concentration into 0.

$$\text{Intrinsic viscosity}[\eta]=\lim(\eta sp/c) \tag{A}$$

wherein c=polymer concentration (g/dL), ηsp=t1/t0−1 (t0: flow time of solvent, t1: flow time of solution).

Ex. 13

(Ex. 13-1) Preparation of $FC(=O)(CF_2)_4C(=O)F$ (Corresponding to Compound (5-1)

Into a 1 L flask, 500 g of $CF_3CF_2CF_2OCF(CF_3)CF_2OCF(CF_3)COO(CF_2)_6—OCOCF(CF_3)OCF_2CF(CF_3)OCF_2CF_2CF_3$ obtained in Ex. 4-2 and 2.1 g of a KF powder were charged, and while vigorously stirring, the flask was heated at 100° C. for 5 hours in an oil bath. At an upper portion of the flask, a reflux condenser adjusted to a temperature of 20° C. was installed. After cooling, a liquid sample was recovered. The liquid sample was purified by distillation. By GC-MS analysis, it was confirmed that the above-identified compound was the main product. The yield was 85 mol %. The yield was obtained by the same method as in Ex. 12-1.

(Ex. 13-2) Preparation of $H_3COC(=O)(CF_2)_4C(=O)OCH_3$ (Corresponding to the Compound (10)

Into a 500 mL flask, 300 g of $FC(=O)(CF_2)_4C(=O)F$ obtained in Ex. 13-1 was charged, and while maintaining the flask at 10° C., 110 g of methanol (corresponding to the compound (9)) was added. After stirring for 2 hours, a potassium hydrochloride aqueous solution was added to recover a lower layer, and the lower layer was purified by distillation. By GC-MS analysis, it was confirmed that the above-identified compound was the main product. The yield of the desired compound as defined in Ex. 12-1 was 87 mol %.

Ex. 14

(Ex. 14-1) Preparation of $FC(=O)(CF_2)_2C(=O)F$ (Corresponding to Compound (5-1)

Into a 1 L flask, 1,000 g of $CF_3CF_2CF_2OCF(CF_3)COO(CF_2)_4OCOCF(CF_3)OCF_2CF_2CF_3$ (corresponding to compound (4-3)) obtained in Ex. 6-2 was charged, and then 6.5 g of a KF powder was charged. While vigorously stirring, the flask was heated at 100° C. for 5 hours in an oil bath. At an upper portion of the flask, a reflux condenser adjusted to a temperature of 20° C. and a gas-collecting fluororesin container were installed in series. After heating, the flask was cooled, and a liquid sample and a gaseous sample were recovered. The liquid sample was purified by distillation. By GC-MS analysis, it was confirmed that the above-identified compound was the main product. The yield was 85 mol %. The yield is mol % of the desired compound contained in a recovered fraction obtained by distillation purification, when the molar number of the desired compound to be theoretically obtained from the charged composition is 100%.

(Ex. 14-2) Preparation of $FC(=O)CF(CF_3)O(CF_2)_3C(=O)F$ (Corresponding to the Compound (7-1)

Into a 2 L autoclave, 500 g of $FOC(CF_2)_2COF$ obtained in Ex. 14-1, 39.1 g of cesium fluoride and 115 g of tetraglyme were charged, and while maintaining the autoclave at −10° C., 470 g of hexafluoropropylene oxide was added. After termination of the reaction, a lower layer was recovered and purified by distillation. By GC-MS, it was confirmed that the above-identified compound was the main product. The yield of the desired compound as defined in Ex. 14-1 was 62 mol %.

(Ex. 14-3) Preparation of $F_2C=CFO(CF_2)_3C(=O)OCH_3$ (Corresponding to the Compound (9-1)

A 1 inch reactor made of Inconel was filled with glass beads so that the filling height would be 20 cm and heated at 250° C. 500 g of $FC(=O)CF(CF_3)O(CF_2)_3C(=O)F$ obtained in Ex. 14-2 was diluted with nitrogen gas so as to be 10 vol % and introduced into the reactor. The linear velocity was controlled at 2.0 cm/s, and while maintaining the passing time of the reaction gas through the glass beads layer to 10 seconds, the reaction was carried out. The reaction outlet gas was collected by means of a dry ice-ethanol trap in which methanol was added. The trap-collected liquid was purified by distillation and analyzed by GC-MS, and as a result, it was confirmed that the above-identified compound was the main product. The yield of the desired compound as defined in Ex. 14-1 was 42 mol %.

INDUSTRIAL APPLICABILITY

According to the process for producing a fluorinated compound of the present invention, the desired perfluorinated compound can be produced at a high yield by a fluorination reaction of a partially fluorinated ester. By using the above compound as a starting material, a fluorinated monomer as a material for a fluorinated resin or an intermediate for a medical adhesive can be provided.

This application is a continuation of PCT Application No. PCT/JP2014/071673 filed on Aug. 19, 2014, which is based upon and claims the benefit of priority from Japanese Patent Application No. 2013-175041 filed on Aug. 26, 2013. The contents of those applications are incorporated herein by reference in their entireties.

What is claimed is:

1. A process for producing a fluorinated compound, the process comprising:
   (I) reacting a compound (1) of formula (1) and a compound (2) of formula (2) to produce a compound (3) of formula (3), wherein a fluorine content is at least 30 mass %;
   (II) fluorinating the compound (3) in a liquid phase to produce a compound (4) of formula (4), $$HOCH_2-R^A-CH_2OH \quad (1)$$

$$X^1C(=O)-C(R^B)(R^C)(R^D) \quad (2)$$

$$(R^D)(R^C)(R^B)C-C(=O)OCH_2-R^A-CH_2OC(=O)-C(R^B)(R^C)(R^D) \quad (3)$$

$$(R^{DF})(R^{CF})(R^{BF})C-C(=O)OCF_2-R^{AF}-CF_2OC(=O)-C(R^{BF})(R^{CF})(R^{DF}) \quad (4)$$

wherein
   $R^A$: a bivalent saturated hydrocarbon group or a partially halogenated bivalent saturated hydrocarbon group,
   $R^B$, $R^C$ and $R^D$: $R^B$ is the same fluorinated monovalent organic group as $R^{BF}$, a monovalent organic group to be converted to $R^{BF}$ by a fluorination reaction, a hydrogen atom or a halogen atom; $R^C$ is the same fluorinated monovalent organic group as $R^{CF}$ or a monovalent organic group to be converted to $R^{CF}$ by a fluorination reaction; and $R^D$ is the same fluorinated monovalent organic group as $R^{DF}$ or a monovalent organic group to be converted to $R^{DF}$ by a fluorination reaction,
   $X^1$: a halogen atom,
   $R^{AF}$: a group having all hydrogen atoms in $R^A$ substituted by fluorine atoms,
   $R^{BF}$: when $R^B$ is a hydrogen atom, $R^{BF}$ is a fluorine atom; when $R^B$ is a halogen atom, $R^{BF}$ is the same halogen atom as $R^B$; and when $R^B$ is neither a hydrogen atom nor a halogen atom, $R^{BF}$ is a fluorinated monovalent organic group which is the same as or different from $R^B$, and when different, $R^{BF}$ is a group which is $R^B$ fluorinated,
   $R^{CF}$: a fluorinated monovalent organic group which is the same as or different from $R^C$, and when different, $R^{CF}$ is a group which is $R^C$ fluorinated, and
   $R^{DF}$: a fluorinated monovalent organic group which is the same as or different from $R^D$, and when different, $R^{DF}$ is a group which is $R^D$ fluorinated;
   (III) subjecting the compound (4) to a cleavage reaction to obtain a compound (5) of formula (5):

$$FC(=O)-R^{AF}-C(=O)F \quad (5); \text{ and}$$

either performing (IVa) and (V) or performing (IVb):
   (IVa) reacting the compound (5) with hexafluoropropylene oxide to obtain a compound (7) of formula (7) and
   (V) heat-decomposing the compound (7) to obtain a compound (8) of formula (8):

$$FC(=O)-CF(CF_3)-O-CF_2-R^{AF}-C(=O)F \quad (7)$$

$$F_2C=CF-O-Q^{AF}-CF=CF_2 \quad (8)$$

wherein
   $Q^{AF}$: when the number of carbon atoms of $R^{AF}$ is 1, $Q^{AF}$ is a single bond; when the number of carbon atoms of $R^{AF}$ is at least 2, $Q^{AF}$ is a group of which the number of carbon atoms is less by 1 than $R^{AF}$ and wherein all hydrogen atoms in a saturated bivalent hydrocarbon group or a partially halogenated bivalent hydrocarbon group are substituted by fluorine atoms; or
   (IVb) reacting the compound (5) with a compound (9) of formula (9) to obtain a compound (10) of formula (10):

$$HO-R \quad (9)$$

$$R-OC(=O)-R^{AF}-C(=O)O-R \quad (10)$$

wherein R is a group selected from the group consisting of $-CH_3$, $-CH_2CH_3$ and $-CH(CH_3)_2$.

2. The process for producing a fluorinated compound according to claim 1, wherein
   the number of carbon atoms of $R^A$ is at most 20, and
   when each of $R^B$, $R^C$ and $R^D$ is the fluorinated monovalent organic group or the monovalent organic group, the number of carbon atoms thereof is at most 10.

3. The process for producing a fluorinated compound according to claim 1, wherein $R^A$ is $(CH_2)_n$, and $R^{AF}$ is $(CF_2)_n$, wherein n is an integer of from 1 to 10.

4. The process for producing a fluorinated compound according to claim 1, wherein
   $R^B$ and $R^{BF}$ are fluorine atoms,
   $R^C$ and $R^{CF}$ are the same $C_{1-3}$ perfluoroalkyl groups, and
   $R^D$ and $R^{DF}$ are the same $C_1$ perfluoroalkyl groups, the same $C_{2-6}$ perfluoroalkoxyl groups or the same $C_{4-8}$ perfluoroalkoxyl groups having one etheric oxygen atom.

5. The process for producing a fluorinated compound according to claim 1, wherein in the fluorinating (II), the fluorination is carried out by supplying a fluorine gas diluted with an inert gas, into the liquid phase, and the proportion of the fluorine gas is from 30 to 60 vol % in the total 100 vol % of the inert gas and the fluorine gas.

6. The process for producing a fluorinated compound according to claim 1, wherein the fluorination is carried out in the liquid phase containing a fluorination reaction solvent, and the fluorination reaction solvent is a fluorinated solvent having no C—H bond and having an etheric oxygen atom.

7. The process for producing a fluorinated compound according to claim 6, wherein the fluorinated solvent is $(R^{DF})(R^{CF})(R^{BF})C-C(=O)F$.

8. The process for producing a fluorinated compound according to claim 1, wherein in the fluorinating (II), the fluorination is carried out in the liquid phase containing a fluorination reaction solvent, and the fluorination reaction solvent is the compound (5).

9. The process for producing a fluorinated compound according to claim 1, the process further comprising:
- (IVa) reacting the compound (5) with hexafluoropropylene oxide to obtain the compound (7) of formula (7) and
- (V) heat-decomposing the compound (7) to obtain the compound (8) of formula (8).

10. The process for producing a fluorinated compound according to claim 1, the process comprising:
- (IVb) reacting the compound (5) with the compound (9) of formula (9) to obtain the compound (10) of formula (10).

11. The process for producing a fluorinated polymer according to claim 9, further comprising:
polymerizing the compound (8).

12. The process for producing a fluorinated compound according to claim 1, wherein the compound (2) is selected from the group consisting of:

$$(CF_3)_2CFC(=O)F \quad (2\text{-}1)$$

$$CF_3CF_2CF_2OCF(CF_3)CF_2OCF(CF_3)C(=O)F \quad (2\text{-}2)$$

$$CF_3CF_2CF_2OCF(CF_3)C(=O)F \quad (2\text{-}3)$$

$$CF_2ClCFClCF_2CF_2OCF(CF_3)C(=O)F \quad (2\text{-}4)$$

$$CF_2BrCF_2OCF(CF_3)C(=O)F \quad (2\text{-}5)$$

$$CF_2ClCFClCF_2CF(CF_3)OCF(CF_3)C(=O)F \quad (2\text{-}6)$$

$$CH_3CH_2CH_2OCF(CF_3)C(=O)F \quad (2\text{-}7).$$

13. The process for producing a fluorinated compound according to claim 12, wherein the compound (1) is:

$$HOCH_2-(CH_2)_n-CH_2OH \quad (1\text{-}1),$$

wherein n is from 2 to 8.

14. The process for producing a fluorinated compound according to claim 1, wherein in the reacting (I), an amount of the compound (2) per the compound (1) is from 2 to 5 times by mole.

15. The process for producing a fluorinated compound according to claim 13, wherein in the reacting (I), an amount of the compound (2) per the compound (1) is from 2 to 5 times by mole.

16. The process for producing a fluorinated compound according to claim 1, wherein the compound (2) is selected from the group consisting of:

$$(CF_3)_2CFC(=O)F \quad (2\text{-}1)$$

$$CF_3CF_2CF_2OCF(CF_3)CF_2OCF(CF_3)C(=O)F \quad (2\text{-}2)$$

$$CF_3CF_2CF_2OCF(CF_3)C(=O)F \quad (2\text{-}3).$$

\* \* \* \* \*